(12) United States Patent
Aram et al.

(10) Patent No.: US 8,002,840 B2
(45) Date of Patent: Aug. 23, 2011

(54) SYSTEMS AND METHODS FOR COMPARTMENTAL REPLACEMENT IN A KNEE

(75) Inventors: Luke Aram, Warsaw, IN (US); Dan Auger, Fort Wayne, IN (US); Adam Hayden, Fort Wayne, IN (US); Jordan Lee, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1114 days.

(21) Appl. No.: 11/170,816

(22) Filed: Jun. 30, 2005

(65) Prior Publication Data
US 2006/0058883 A1    Mar. 16, 2006

Related U.S. Application Data

(63) Continuation-in-part of application No. 11/033,614, filed on Jan. 12, 2005, now Pat. No. 7,258,701.

(60) Provisional application No. 60/535,967, filed on Jan. 12, 2004.

(51) Int. Cl.
*A61F 2/38* (2006.01)

(52) U.S. Cl. .................................................. 623/20.15

(58) Field of Classification Search ..... 623/20.14–20.36
See application file for complete search history.

(56) References Cited

U.S. PATENT DOCUMENTS

| | | | |
|---|---|---|---|
| 3,798,679 A | 3/1974 | Ewald | |
| 3,816,855 A | 6/1974 | Saleh | |
| 3,852,830 A | 12/1974 | Marmor | |
| 3,949,428 A | 4/1976 | Cavendish et al. | |
| 3,953,899 A | 5/1976 | Charnley | |
| 4,001,896 A | 1/1977 | Arkangel | |
| 4,034,418 A | 7/1977 | Jackson et al. | |
| 4,151,615 A | 5/1979 | Hall | |
| 4,178,641 A | 12/1979 | Grundei et al. | |
| 4,207,627 A | 6/1980 | Cloutier | |
| 4,209,861 A | 7/1980 | Walker et al. | |
| 4,216,549 A | 8/1980 | Hillberry et al. | |
| 4,217,666 A | 8/1980 | Averill | |
| 4,224,696 A | 9/1980 | Murray et al. | |
| 4,309,778 A | 1/1982 | Buechel et al. | |
| 4,340,978 A | 7/1982 | Buechel et al. | |
| 4,457,307 A | 7/1984 | Stillwell | |

(Continued)

FOREIGN PATENT DOCUMENTS

DE    29 01 009    7/1980

(Continued)

OTHER PUBLICATIONS

Richards, KA-012255, Richards Mod II Knee, 1976 (56 pages).

(Continued)

*Primary Examiner* — Bruce E Snow
(74) *Attorney, Agent, or Firm* — Maginot, Moore & Beck

(57) ABSTRACT

A prosthesis system includes a first component having an outer surface, an inner surface, a first side and a second side, the first component configured to replace a first portion of a surface of a bone. A second component is configured to replace a second portion of the surface of the bone and a spacer is configured to be located adjacent to the first side of the first component and between the first component and the second component when the first component and the second component replace the first portion and second portion, respectively, of the surface of the bone.

21 Claims, 30 Drawing Sheets

U.S. PATENT DOCUMENTS

| | | | |
|---|---|---|---|
| 4,462,120 A | 7/1984 | Rambert et al. | |
| 4,470,158 A | 9/1984 | Pappas et al. | |
| 4,568,348 A | 2/1986 | Johnson et al. | |
| 4,574,794 A | 3/1986 | Cooke et al. | |
| 4,586,933 A | 5/1986 | Shoji et al. | |
| 4,770,663 A | 9/1988 | Hanslik et al. | |
| 4,822,366 A | 4/1989 | Bolesky | |
| 4,936,847 A * | 6/1990 | Manginelli | 623/20.16 |
| 4,950,298 A | 8/1990 | Gustilo et al. | |
| 5,021,061 A | 6/1991 | Wevers et al. | |
| 5,092,895 A | 3/1992 | Albrektsson et al. | |
| 5,100,409 A | 3/1992 | Coates et al. | |
| 5,116,375 A | 5/1992 | Hofmann | |
| 5,123,927 A | 6/1992 | Duncan et al. | |
| 5,147,406 A | 9/1992 | Houston et al. | |
| 5,152,796 A | 10/1992 | Slamin | |
| 5,171,282 A | 12/1992 | Pequignot | |
| 5,181,925 A | 1/1993 | Houston et al. | |
| 5,203,807 A | 4/1993 | Evans et al. | |
| 5,219,362 A | 6/1993 | Tuke et al. | |
| 5,226,916 A | 7/1993 | Goodfellow et al. | |
| 5,282,866 A | 2/1994 | Cohen et al. | |
| 5,326,359 A | 7/1994 | Oudard | |
| 5,358,527 A | 10/1994 | Forte | |
| 5,358,529 A | 10/1994 | Davidson | |
| 5,358,531 A | 10/1994 | Goodfellow et al. | |
| 5,370,699 A | 12/1994 | Hood et al. | |
| 5,395,401 A | 3/1995 | Bahler | |
| 5,405,395 A | 4/1995 | Coates | |
| 5,405,398 A | 4/1995 | Buford, III et al. | |
| 5,413,604 A | 5/1995 | Hodge | |
| 5,549,684 A | 8/1996 | Amino et al. | |
| 5,549,685 A | 8/1996 | Hayes | |
| 5,549,688 A | 8/1996 | Ries et al. | |
| 5,556,433 A | 9/1996 | Gabriel et al. | |
| 5,569,259 A | 10/1996 | Ferrante et al. | |
| 5,609,639 A | 3/1997 | Walker | |
| 5,702,466 A | 12/1997 | Pappas et al. | |
| 5,725,584 A | 3/1998 | Walker et al. | |
| 5,728,162 A | 3/1998 | Eckhoff | |
| 5,755,800 A | 5/1998 | O'Neil et al. | |
| 5,755,803 A | 5/1998 | Haines et al. | |
| 5,766,255 A | 6/1998 | Slamin et al. | |
| 5,769,855 A | 6/1998 | Bertin et al. | |
| 5,782,925 A | 7/1998 | Collazo et al. | |
| 5,824,105 A | 10/1998 | Ries et al. | |
| 5,871,541 A | 2/1999 | Gerber | |
| 5,871,545 A | 2/1999 | Goodfellow et al. | |
| 5,902,339 A | 5/1999 | Keller | |
| 5,906,643 A | 5/1999 | Walker | |
| 5,964,808 A | 10/1999 | Blaha et al. | |
| 5,984,969 A | 11/1999 | Matthews et al. | |
| 6,013,103 A | 1/2000 | Kaufman et al. | |
| 6,123,729 A | 9/2000 | Insall et al. | |
| 6,126,693 A | 10/2000 | O'Neil et al. | |
| 6,139,580 A | 10/2000 | Wurzinger et al. | |
| 6,165,223 A | 12/2000 | Metzger et al. | |
| 6,168,629 B1 | 1/2001 | Timoteo | |
| 6,171,340 B1 | 1/2001 | McDowell | |
| 6,171,640 B1 | 1/2001 | Bringe | |
| 6,190,415 B1 | 2/2001 | Cooke et al. | |
| 6,197,064 B1 | 3/2001 | Haines et al. | |
| 6,214,051 B1 | 4/2001 | Bädorf et al. | |
| 6,214,052 B1 | 4/2001 | Burkinshaw | |
| 6,214,952 B1 | 4/2001 | Sadatoshi et al. | |
| 6,231,611 B1 | 5/2001 | Mosseri | |
| 6,235,060 B1 | 5/2001 | Kubein-Meesenburg et al. | |
| 6,245,110 B1 | 6/2001 | Grundei et al. | |
| 6,299,645 B1 | 10/2001 | Ogden | |
| 6,364,911 B1 | 4/2002 | Schmotzer et al. | |
| 6,383,222 B1 | 5/2002 | Bädorf | |
| 6,416,552 B1 | 7/2002 | Hoeppner et al. | |
| 6,520,964 B2 | 2/2003 | Tallarida et al. | |
| 6,527,807 B1 | 3/2003 | O'Neil et al. | |
| 6,554,866 B1 | 4/2003 | Aicher et al. | |
| 6,582,469 B1 | 6/2003 | Tornier | |
| 6,589,283 B1 | 7/2003 | Metzger et al. | |
| 6,616,696 B1 | 9/2003 | Merchant | |
| 6,652,587 B2 | 11/2003 | Felt et al. | |
| 6,712,856 B1 | 3/2004 | Carignan et al. | |
| 6,726,723 B2 | 4/2004 | Running | |
| 6,743,258 B1 | 6/2004 | Keller | |
| 6,866,684 B2 | 3/2005 | Fell et al. | |
| 6,893,467 B1 | 5/2005 | Bercovy | |
| 7,297,164 B2 * | 11/2007 | Johnson et al. | 623/20.14 |
| 2002/0138150 A1 | 9/2002 | Leclercq | |
| 2002/0198528 A1 | 12/2002 | Engh et al. | |
| 2003/0078661 A1 | 4/2003 | Houfburg | |
| 2003/0093152 A1 | 5/2003 | Pedersen et al. | |
| 2003/0158606 A1 * | 8/2003 | Coon et al. | 623/20.15 |
| 2003/0225457 A1 | 12/2003 | Justin et al. | |
| 2003/0225458 A1 | 12/2003 | Donkers et al. | |
| 2003/0233148 A1 | 12/2003 | Ferree | |
| 2004/0249462 A1 | 12/2004 | Huang | |
| 2005/0027363 A1 | 2/2005 | Gordon | |
| 2005/0049710 A1 | 3/2005 | O'Driscoll et al. | |
| 2005/0055025 A1 | 3/2005 | Zacouto et al. | |
| 2005/0089365 A1 | 4/2005 | Despres et al. | |

FOREIGN PATENT DOCUMENTS

| | | |
|---|---|---|
| DE | 33 05 237 A1 | 8/1983 |
| DE | 29 54 475 | 12/1986 |
| EP | 0 824 904 | 2/1980 |
| EP | 0 346 183 A1 | 12/1989 |
| EP | 0 437 390 | 7/1991 |
| EP | 0 567 705 A1 | 11/1993 |
| EP | 0 600 806 | 6/1994 |
| EP | 0 634 155 | 1/1995 |
| EP | 0 674 887 | 10/1995 |
| EP | 0 749 734 | 12/1996 |
| EP | 1 099 430 | 5/2001 |
| EP | 1 493 408 | 1/2005 |
| FR | 2 589 720 | 11/1985 |
| FR | 2 621 243 | 10/1987 |
| FR | 2 768 329 | 3/1999 |
| FR | 2 682 287 A1 | 10/2001 |
| GB | 2 215 610 A | 9/1989 |
| GB | 2 355 935 A | 5/2001 |
| JP | 2003/070127 A | 3/2003 |
| WO | WO 79/00 739 | 10/1979 |
| WO | WO 87/02882 A1 | 5/1987 |
| WO | WO 95/14446 A1 | 6/1995 |
| WO | WO 98/20818 A1 | 5/1998 |
| WO | WO 99/13803 A2 | 3/1999 |
| WO | WO 00/23010 A1 | 4/2000 |
| WO | WO 00/23011 | 4/2000 |
| WO | WO 00/44316 | 8/2000 |
| WO | WO 03/070127 | 8/2003 |
| WO | WO 2004/037119 | 5/2004 |

OTHER PUBLICATIONS

Richards Modular Knee System (pp. 35-59, "The Type II Femoral Component may also be used in patello-femoral replacement done in conjunction with unicondylar total knee devices on ether or both condyles," Richards, Orthopedic Catalog, 1979(6 pages).

Maxim, "The Complete Knee System," Biomet, Inc., 1995 (15 pages).

Shoji et al., "Failed Polycentric Total Knee Prostheses," The Journal of Bone and Joint Surgery, vol. 58-A, No. 6, pp. 773-777, Sep. 1976, (5 pages).

Bourne et al., "Kinematic 1 and 2 Oxford Knee Arthroplasty—A 5-8-year Follow-Up Study," The Journal of Arthroplasty, No. 4, pp. 285-291, Dec. 1987 (7 pages).

Arciero et al., "Patellofemoral Arthroplasty: A Three-to-Nine Year Follow-Up Study," Clinical Orthopaedics and Related Research, No. 236, pp. 60-71, Nov. 1988, (12 pages).

Buechel and Pappas, "New Jersey Low Contact Stress Knee Replacement System," Surgical Reconstruction of the Arthritic Knee II, pp. 147-177, 1989(31 pages).

Stockley et al., "Bicondylar St. George Sledge Knee Arthroplasty," Clinical Orthopaedics and Related Research, No. 255, pp. 228-234, Jun. 1990, (7 pages).

Fink et al., Z Orthop Ire Grenzgeb, "The femoropatellar endoprosthesis—still of value today?," Z. Orthop Ihre Grenzbeg, 137(3), pp. 247-252 May/Jun. 1999, 1999 (7 pages).

Seedhom BB, et al., "Designing a total knee prosthesis," Engineering in Med. 1:28, pp. 28-32 1972 (5 pages).

Seedhom BB, et al., "A Technique for the Study of Geometry and Contact in Normal and Artificial Knee Joints," Wear, 20, pp. 189-199, 1972 (11 pages).

Seedhom BB, et al., "The Leeds Knee," Institution Mechanical Engineers, 1974 (7 pages).

Cartier et al., "Patellofemoral Arthroplasty—2-12-year Follow-Up Study," The Journal of Arthroplasty, vol. 5 No. 1, pp. 49-54, Mar. 1990 (7 pages).

Argenson et al., "Is There a Place for Patellofemoral Arthroplasty," Clinical Orthopaedics and Related Research, No. 321, pp. 162-167, 1995 (7 pages).

Product Brochure for LCS PFJ Prosthesis, published by DePuy Orthopaedics, Inc., 2000 (2 pages).

Surgical Technique for LCS PFJ Prosthesis, published by DePuy Orthopaedics, Inc., 2000 (12 pages).

Orthopaedics Surgical Technique for LCS PFJ Prosthesis, published by DePuy Orthopaedics, Inc., 2000 (12 pages).

Reference Guide and Surgical Technique for Patella Planing System, published by DePuy Orthopaedics, Inc., 2000 (15 pages).

Product Rationale for LCS UNI, published by DePuy Orthopaedics, Inc., 1998 (8 pages).

Surgical Technique for LCS UNI, published by DePuy Orthopaedics, Inc., 1998 (13 pages).

Product Brochure for Preservation Uni-compartmental Knee, published by DePuy Orthopaedics, Inc., 2002 (4 pages).

Surgical Technique for Preservation Uni-compartmental Knee, published by DePuy Orthopaedics, Inc., 2002 (31 pages).

* cited by examiner

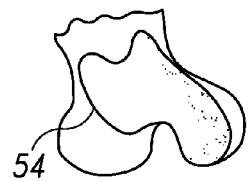
Fig. 5
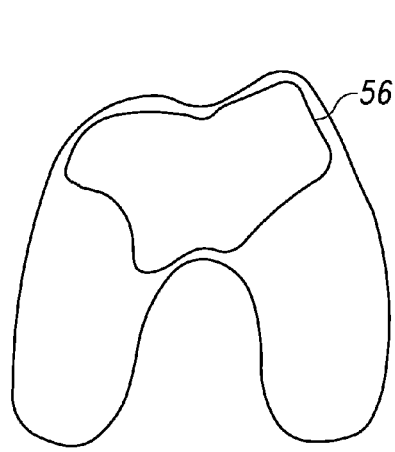 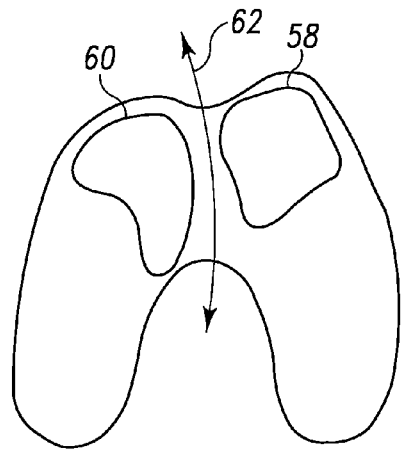
Fig. 6  Fig. 7

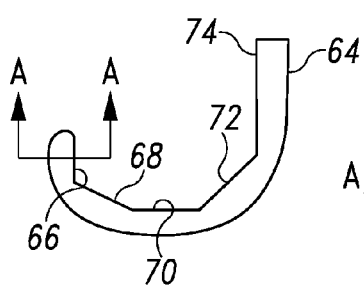
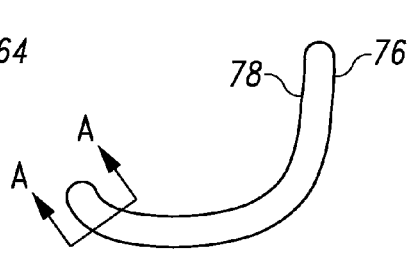
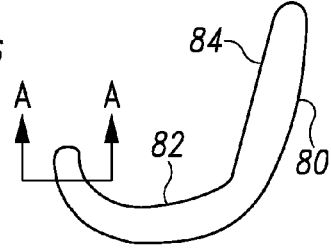
Fig. 8　　　Fig. 9　　　Fig. 10
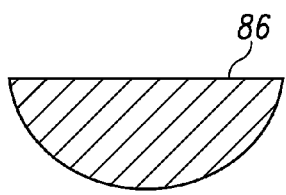
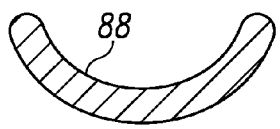
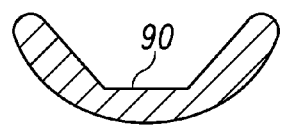
Fig. 11A　　Fig. 11B　　Fig. 11C
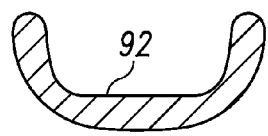
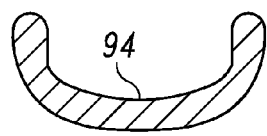
Fig. 11D　　Fig. 11E

SECTION A-A

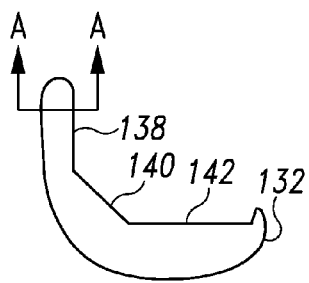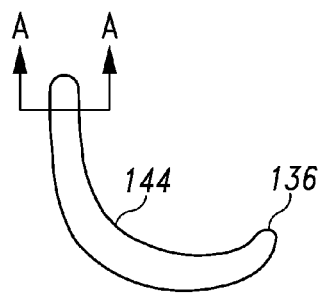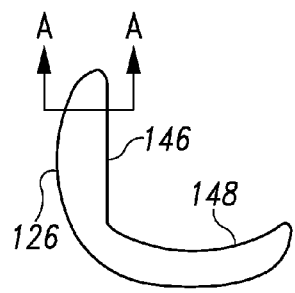
Fig. 22    Fig. 23    Fig. 24
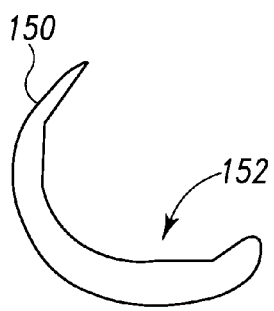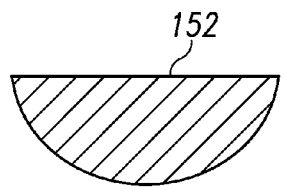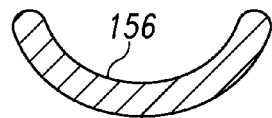
Fig. 25    Fig. 26A    Fig. 26B
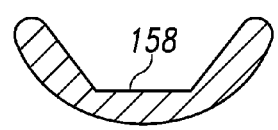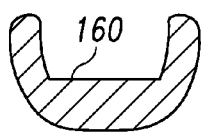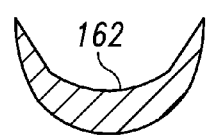
Fig. 26C    Fig. 26D    Fig. 26E

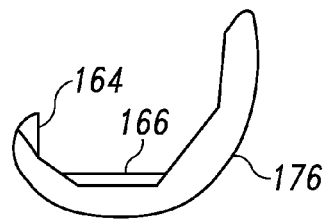
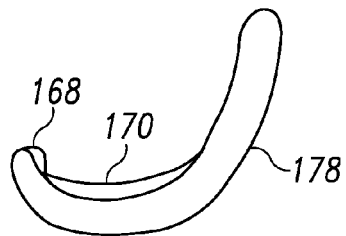
Fig. 27  Fig. 28
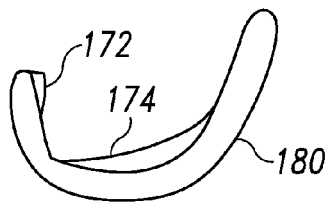
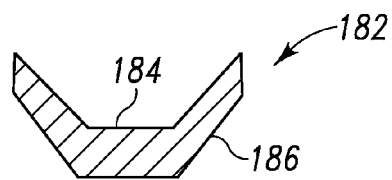
Fig. 29  Fig. 30A
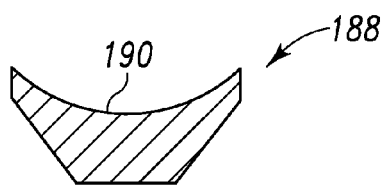
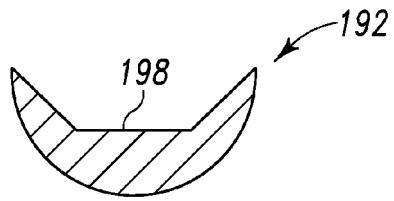
Fig. 30B  Fig. 30C
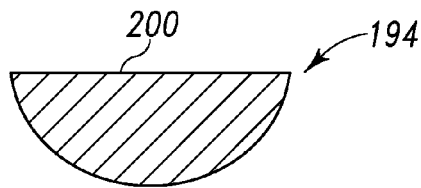
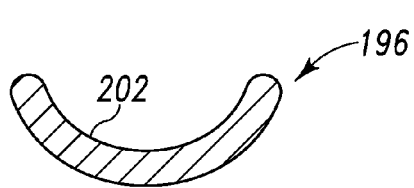
Fig. 30D  Fig. 30E

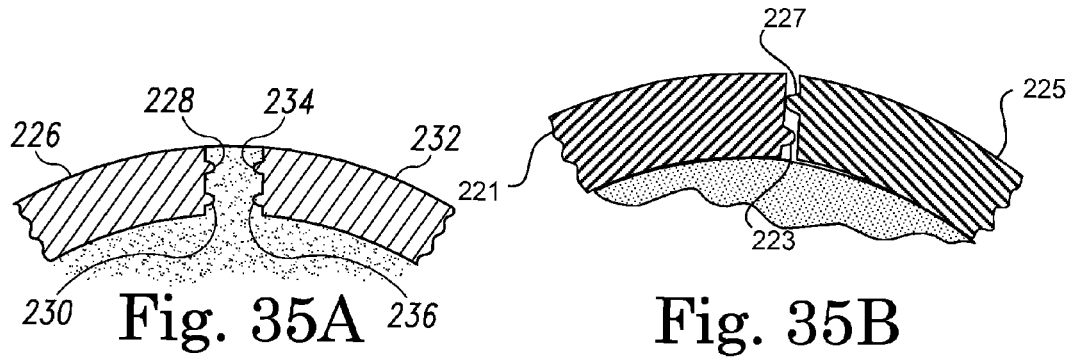
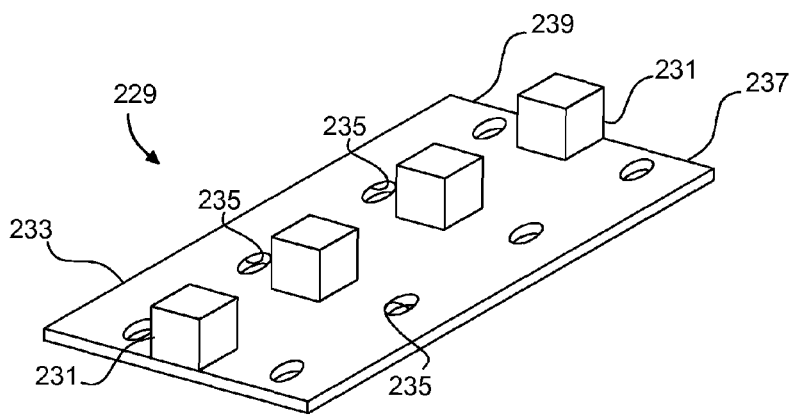
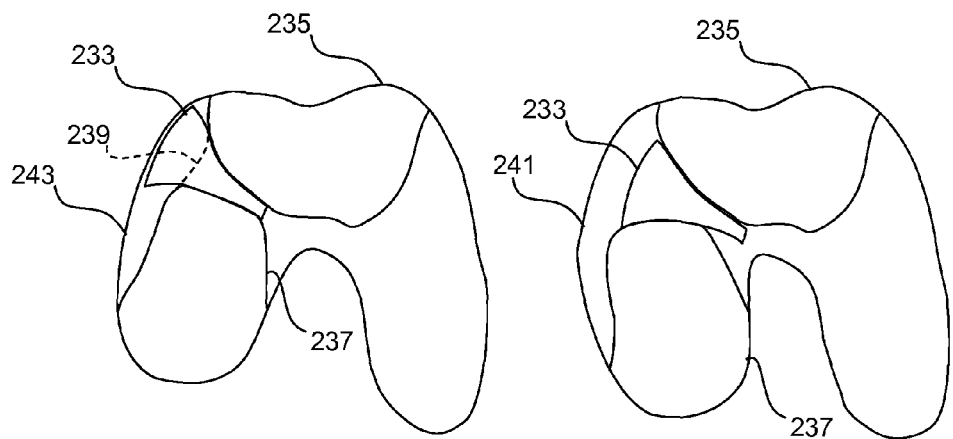
Fig. 35D    Fig. 35E

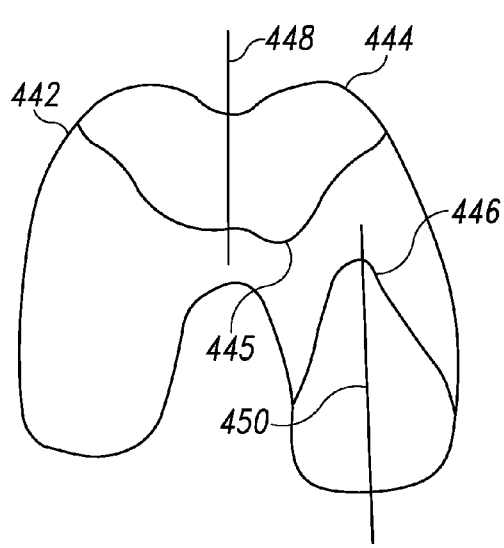
Fig. 64
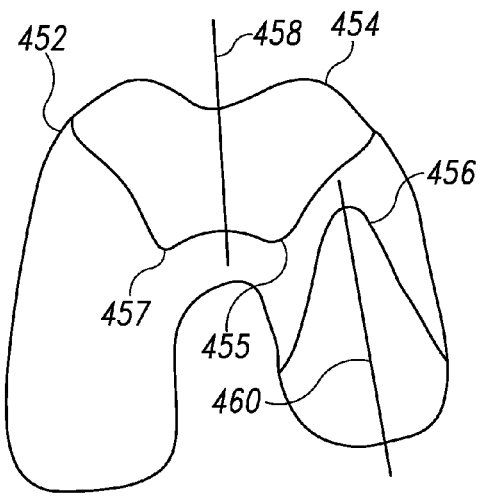
Fig. 65
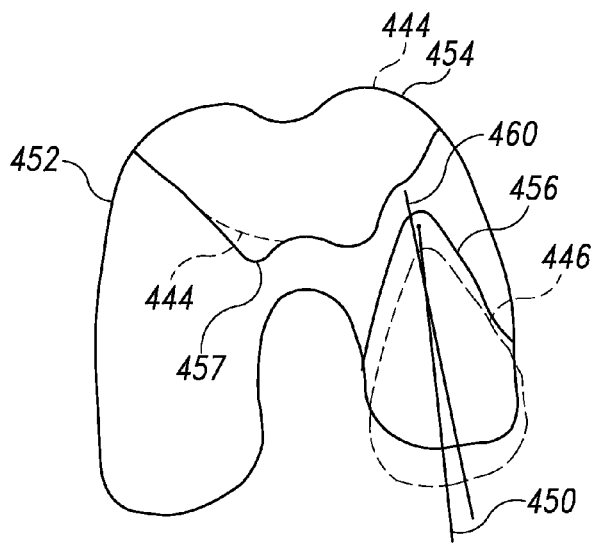
Fig. 66
Fig. 67

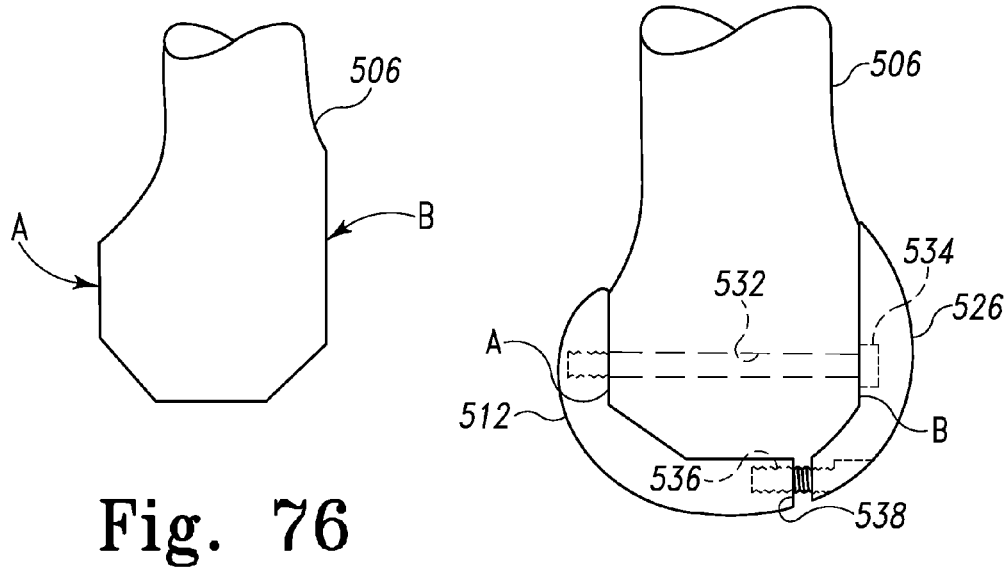
Fig. 76
Fig. 77
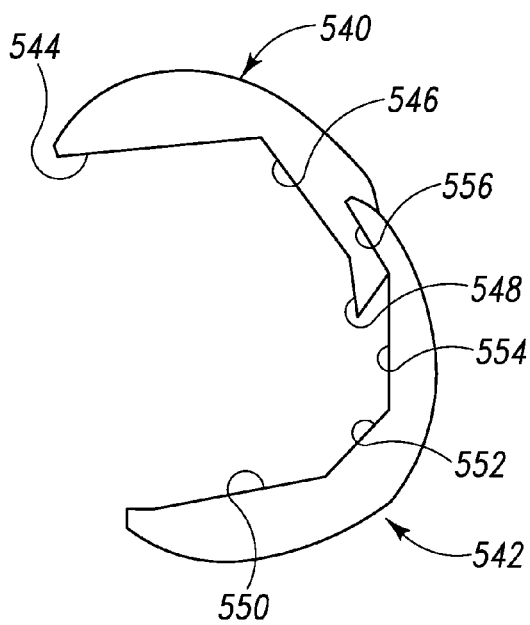
Fig. 78

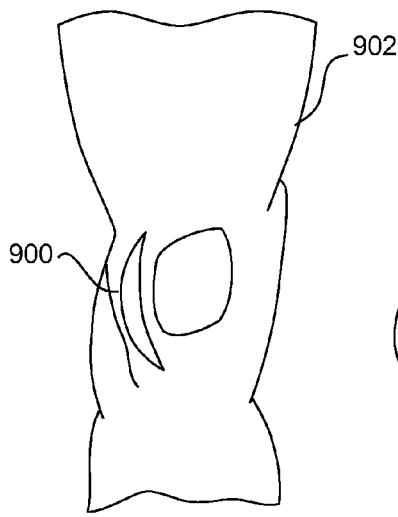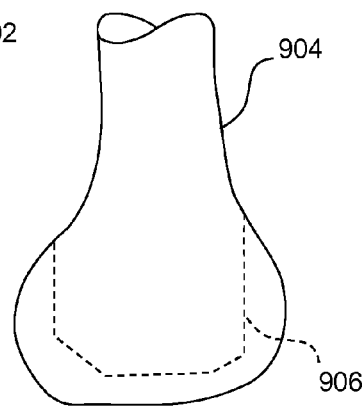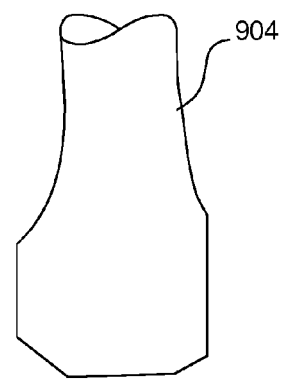
Fig. 80B    Fig. 80C
Fig. 80A
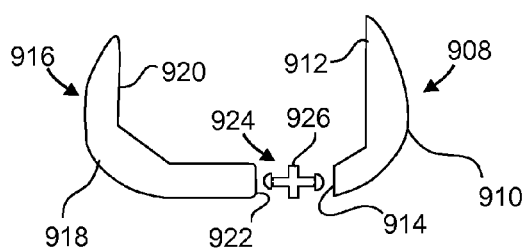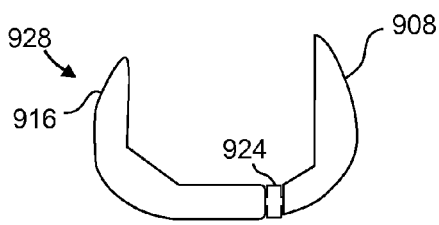
Fig. 80E
Fig. 80D
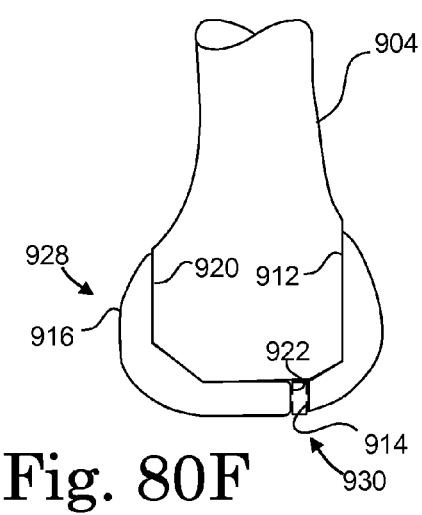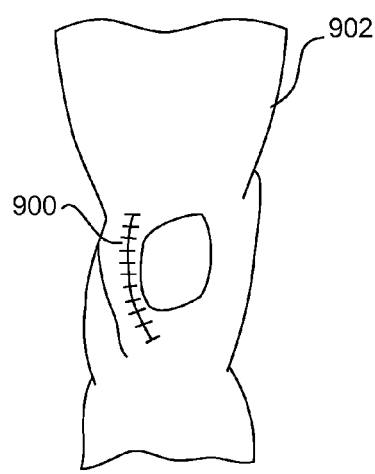
Fig. 80F    Fig. 80G

SYSTEMS AND METHODS FOR COMPARTMENTAL REPLACEMENT IN A KNEE

This application is a continuation in part of U.S. application Ser. No. 11/033,614 filed Jan. 12, 2005 which in turn claims priority to U.S. provisional application No. 60/535,967 filed Jan. 12, 2004.

FIELD OF THE INVENTION

This invention relates generally to prosthesis for human body joints, and, more particularly, to prosthesis for knees.

BACKGROUND OF THE INVENTION

Total knee replacement (TKR) surgery and component systems for replacing compartments of a knee in total replacement surgery are well-known. Typically, the surgery involves resecting the distal end of a femur so a femoral component may be mounted to the femur. The femoral component replaces the lateral condyle, medial condyle, and patellofemoral portions of the femur because one or more of these areas of the knee are diseased and are no longer wearing well or providing an adequate range of motion for a patient.

In TKR surgery, the proximal end of the tibia is also resected so that a tibial component may be mounted to the tibia to receive the lateral and medial condyles of the femoral component. The tibial component may be comprised of a material having a low coefficient of friction to simulate the meniscus being replaced by the tibial component.

Thus, a TKR system includes components for use in three compartments: the medial tibial femoral compartment, the lateral tibial femoral compartment and the patella femoral compartment, for which the opposing areas of the femur, tibia and patella are prepared for mounting.

U.S. Pat. No. 3,816,855 discloses one such system. The '855 patent discloses a unitary femoral component in the form of a shell with two condylar portions. The outer surface of the shell is formed to conform to the natural shapings of the corresponding parts of the knee joint. The inner surface of the shell mirrors this shape, presenting a surface that is curved in the medial lateral direction as well as the anterior posterior direction. While providing a number of benefits, the device of the '855 patent suffers from several limitations.

The preparation of a subject for TKR surgery usually causes substantial trauma. A large incision is required for insertion of all of the components of a TKR system and the bone resection required for mounting of the components may require extensive recovery time. Thus, single piece replacement components such as the device of the '855 patent require a large incision.

In an effort to reduce this trauma, and accordingly, reduce the recovery time associated with such surgery, TKR systems have been developed that provide TKR components in parts that mate to form the larger TKR components.

U.S. Patent Application No. US 2003/0158606 discloses such a system of TKR components. As shown in that application, the femoral component may consist of two or three pieces. Each of these pieces is smaller than the femoral component that they form when they are assembled in the knee. As a result, the incision required for insertion of these pieces is smaller than an incision for a femoral component having all of these pieces in a single component. Likewise, the tibial component consists of two parts, each of which is smaller than the tibial component that they form when assembled in the knee.

U.S. Patent Application No. US 2002/0138150 A1 discloses an alternative two-piece femoral component that allows a center part and a condyle part to be pushed onto a femur separately during implantation. The different parts are then joined according to conventional means. The device of the '150 application further describes guides that are intended to aid in tracking of the patella during extreme flexion.

However, both the '606 application and the '150 application use traditional methods of attaching the replacement components to the femur. Such methods are subject to problems as the replacement component is exposed to various stresses and impacts. One such problem is the eventual loosening of the components. When one component loosens, adjacent components may rub together, generating frictional debris and premature failure of the components.

Yet another limitation of implant systems is that as a commercial consideration, many replacement components are mass-produced. While beneficially lowering the cost of implants, these systems are generally provided in a limited number of discrete sizes that most likely will not be precisely the size needed for a patient. For example, a patient's femur may measure 75-mm in diameter. However, available implants for this patient may measure 70-mm and 80-mm. Thus, a surgeon must replace the natural femur with a component that is either too large or too small.

What is needed is a system and method for performing TKR surgery so that pieces of a compartment may be inserted through an incision independently.

What is needed is a system and method of implanting femoral components that more closely reflects the size of the natural femur.

What is needed is a system and a method of implanting femoral components that allow the size of the joined components to be individualized.

What is needed is a system and a method of implanting femoral components that reduce the generation of wear material from the components.

SUMMARY OF THE INVENTION

The above described needs are met by a system and method that operate in accordance with the principles of the present invention. In one embodiment, the system includes a prosthesis system includes a first component having an outer surface, an inner surface, a first side and a second side, the first component configured to replace a first portion of a surface of a bone. A second component is configured to replace a second portion of the surface of the bone and a spacer is configured to be located adjacent to the first side of the first component and between the first component and the second component when the first component and the second component replace the first portion and second portion, respectively, of the surface of the bone.

In a further embodiment, a prosthesis system includes a patellofemoral component configured to replace a portion of a patellofemoral surface of a bone and a first shim configured to replace a surface portion of the bone adjacent to a first side of the patellofemoral component.

In yet another embodiment, a femoral prosthesis system includes a patellofemoral joint component having an edge and configured to replace a portion of a patellofemoral joint bearing surface. The system further includes a spacer having a first edge portion and a second edge portion, the first edge portion configured to be located adjacent to the edge of the patellofemoral joint component and a condylar component configured to be located adjacent to the second edge portion spacer and to replace a portion of a condylar bearing surface.

The above-described features and advantages, as well as others, will become more readily apparent to those of ordinary skill in the art by reference to the following detailed description and accompanying drawings.

BRIEF DESCRIPTION OF THE DRAWINGS

FIGS. 5, 6 and 7 depict exemplary configurations of medial tibial femoral, lateral tibial femoral and PFJ components in a system of the present invention;

FIGS. 8, 9 and 10 depict various configurations of the interior of PFJ/condylar components in the anterior to posterior direction in a system of the present invention;

FIGS. 11A, 11B, 11C, 11D and 11E depict various configurations of the interior of PFJ/condylar components in the medial to lateral direction in a system of the present invention;

FIGS. 22, 23 and 24 depict embodiments of condyle components with a faceted interior, a combined flat and curved interior, and a curved interior in the anterior to posterior direction that may be used in a system of the present invention;

FIG. 22 depicts an embodiment of a condyle component with a faceted interior in the anterior to posterior direction that may be used in a system of the present invention;

FIG. 23 depicts an embodiment of a condyle component with a curved interior in the anterior to posterior direction that may be used in a system of the present invention;

FIG. 24 depicts an embodiment of a condyle component with a combined flat and curved interior in the anterior to posterior direction that may be used in a system of the present invention;

FIG. 25 depicts an embodiment of a condyle component with a faceted interior in the anterior to posterior direction and a posterior extension that may be used in a system of the present invention;

FIGS. 26A, 26B, 26C, 26D and 26E depict various cross-sections in the medial to lateral direction that may be used in the condyle components of FIGS. 22, 23, 24 and 25;

FIGS. 27, 28 and 29 depict embodiments of augments shaped to fit various internal anterior to posterior geometries of components that may be used in a system of the present invention;

FIGS. 30A, 30B, 30C, 30D and 30E depict various cross-sections in the medial to lateral direction that may be used in the augments of FIGS. 27, 28 and 29;

FIG. 35A depicts a beaded spacer structure at the interface between components and a bone tide that may be used in a system of the present invention;

FIG. 35B depicts a beaded spacer structure at the interface between two components that may be used in a system of the present invention wherein the spacer beads are complimentarily attached to both of the components;

FIG. 35C depicts an alternative spacer structure with flaps which is configurable for a specific application that may be used in a system of the present invention;

FIG. 35D depicts a patient configuration of a shim spacer structure at the interface between two components that may be used in a system of the present invention to allow components to be used in a variety of patient configurations;

FIG. 35E depicts the shim spacer structure and components of FIG. 35D configured for a patient geometry different than the configuration of FIG. 35D;

FIG. 64 depicts components implanted in a femur in optimized positions with respect to patellar and tibial load lines;

FIG. 65 depicts components identical to the components of FIG. 64 implanted in a femur in optimized positions with respect to patellar and tibial load lines;

FIG. 66 depicts the different orientations between the components of FIG. 64 and the components of FIG. 65 that are possible with components that may be used in a system of the present invention;

FIG. 67 depicts a femoral component of a knee replacement that may be used in a system of the present invention;

FIG. 76 depicts the femur of FIGS. 73 and 75 with the anterior, posterior and distal portions resected;

FIG. 77 depicts the femur of FIG. 76 implanted with the components of FIG. 74 in accordance with the present invention;

FIG. 78 depicts components with some interior surfaces that are parallel to each other that may be used in accordance with the present invention;

FIGS. 80A-G depict an implantation procedure for a prosthesis system that is connected ex vivo in accordance with the present invention.

DETAILED DESCRIPTION OF THE INVENTION

Individual Components

Figure 1:
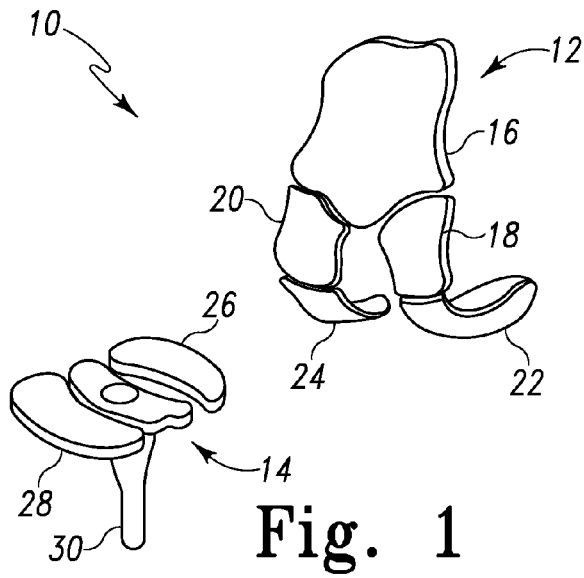
FIG. 1 depicts a patella femoral component and a tibial femoral component that may be included in a system made in accordance with principles of the present invention.

FIG. 1 shows a system 10 that is comprised of a femoral replacement 12, a tibial replacement 14, and a patellar replacement (not shown). The femoral replacement 12 includes a patellofemoral joint (PFJ) component 16, an upper lateral condyle component 18, an upper medial condyle component 20, a lateral femoral anterior/posterior condyle component 22, and a medial femoral anterior/posterior condyle component 24. In accordance with one embodiment (not shown) the upper condyle components and femoral anterior/posterior condyle components are provided as a single component. The tibial replacement 14 includes a medial meniscus component 26, a lateral meniscus component 28, and a tibial stem component 30.

By segmenting the replacements into upper and anterior-posterior medial, and lateral, PFJ, meniscus and tibial stem components, the system 10 of the present invention enables a surgeon to remove only the diseased portion of a femur or tibia and implant the corresponding component to perform a partial knee replacement. Because the components are smaller than a one-piece construction of the total implant, the incision for the implantation surgery is smaller and the recovery time from the surgery, correspondingly, reduced.

Additionally, the replacements allow for complimentary implantation. "Complimentary" replacement components, as used herein, are defined to be components that can be used independently and/or jointly, such that there is no need to remove previously implanted components if additional components are needed at a later time. Furthermore, the complimentary components need not align with one another in a particular orientation after implantation because the components are not shaped to require assembly with adjacent components into a unitary piece. Instead, the surgeon is free to locate a replacement component in accordance with the conditions of a particular bone area. Accordingly, the surgeon need not compromise on local geometry accommodation in order to achieve an overall fit for the component. Thus, the system 10 enables more freedom of movement and orientation of the knee replacement components than has been available with previous compartment replacements.

Because the components are both segmented and complimentary, a surgeon may replace only the diseased portion of a bone which may be limited to a single area of the femur. At some later time, if the bone further deteriorates, the further deteriorated portion of the bone may be replaced without the need to remove the initially implanted component.

For example, a surgeon may first implant only the PFJ component 16 during a first surgical procedure. Some time later, perhaps years later, the upper medial condylar area may be determined to need replacement. In accordance with the principles of the present invention, a surgeon need only implant the upper medial condyle component 20 adjacent to the previously implanted PFJ component 16.

Those of ordinary skill in the art will appreciate that any of the components shown in FIG. 1 may be implanted in a number of different sequences and combinations in a number of different surgical procedures. Thus, the anterior/posterior condyle component 24 may be implanted first, with the PFJ component 16 implanted during a later procedure, and the upper medial condyle component 20 implanted during a still later procedure. Alternatively, all of the components shown in FIG. 1 may be implanted during a single procedure. Moreover, if one implanted component were to become damaged or worn, the single component may be replaced without disturbing other implanted components.

Partial Unibody Components

Figure 2:
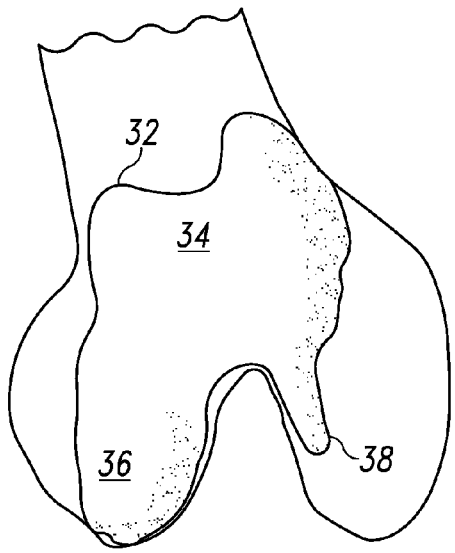
FIGS. 2 and 3 depict exemplary configurations of medial tibial femoral, lateral tibial femoral and patella femoral joint (PFJ) components with trochlear extensions in a system of the present invention.
Figure 3:
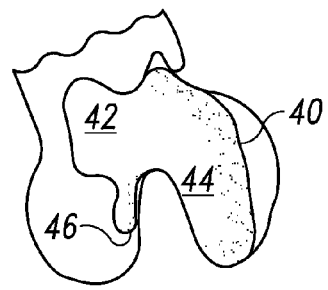

To accommodate various arrangements, the patellofemoral joint component 16, the upper medial condyle component 20, and/or the upper lateral condyle component 18 may be configured as a partial unibody component. As shown in FIG. 2, a PFJ/medial condyle component 32 includes a PFJ area 34 and a medial condyle area 36 in a single piece. The PFJ/medial condyle component 32 may also include a trochlear extension area 38. FIG. 3 depicts a PFJ/lateral condyle component 40 having a PFJ area 42, a lateral condyle area 44, and a medial trochlear extension area 46.

The lateral trochlear extension area 38 and the medial trochlear extension area 46 enhance patella tracking. In flexion beyond 90 degrees, the patella begins to ride over the trochlear notch in a femur. When portions of the femur have been replaced, incongruities near the trochlear notch facilitate dislocation of the patella as the patella begins to ride over the trochlear notch. The trochlear extensions permit the patella to articulate over the replacement component beyond 90 degrees of flexion without dislocation. A lateral trochlear extension area is particularly important because the patella tends to sublux laterally during such flexion beyond 90 degrees. However, the relatively large lateral trochlear extension area 38 and medial trochlear extension area 46 constrain the potential placement of condylar components.

Figure 4:
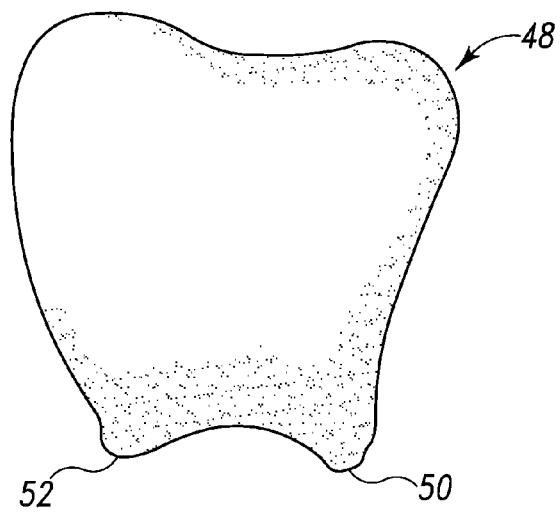
FIG. 4 depicts an exemplary configuration of a PFJ component with nodes in a system of the present invention.

Provision of enhanced tracking without excessive constraints on the placement of condylar components is accomplished by the PFJ component 48 shown in FIG. 4. The PFJ component 48 includes the nodes 50 and 52. The nodes 50 and 52 extend outwardly from the main portion of the PFJ component 48 to a lesser extent than the lateral trochlear extension area 38 and medial trochlear extension area 46 extend from the PFJ/medial condyle components 32 and 40, respectively. Thus, a condylar component may be placed adjacent to the PFJ component 48 in a number of different orientations.

Of course, the medial trochlear extension area 46 may be replaced with a node. Alternatively, as shown in FIG. 5, a PFJ/medial condyle component 54 may be made without any medial trochlear area. Likewise, a PFJ/medial condyle component may be made with a node or without a lateral trochlear area.

A unitary component may be of substantially smaller size than the unitary components depicted above. By way of example, FIG. 6 shows a partial unitary component 56 that extends across most of the PFJ area. However, the minimum desired size of partial unitary component is a function of the size of the bone that needs to be replaced. Thus, a unitary component may be fashioned to be substantially smaller than the partial unitary component 56. One such example is the partial unitary component 58 which is shown in FIG. 7. The partial unitary component 58 is generally in the shape of the partial unitary component 56 along the right side of the components as viewed in FIGS. 6 and 7. However, the partial unitary component 58 is much smaller than the partial unitary component 56.

In the event that a second area of bone needs to be replaced, another unitary component may be provided as shown by the partial unitary component 60. The partial unitary components 58 and 60 are effectively a multi-piece version of the partial unitary component 56, with a gap provided between the partial unitary components 58 and 60 when they are implanted. Those of ordinary skill in the relevant art will appreciate that additional partial unitary components of varying size may be provided within the scope of the present invention.

A consideration in planning for multi-piece replacement components, however, is that it is typically desired to avoid splitting partial unitary components along load lines. A load line indicates an area that experiences higher load as a joint moves between flexion and extension. One such load line is shown in FIG. 7 as the load line 62. In this embodiment, the partial unitary components 58 and 60 have been selected such that the load line 62 extends over the bone that remains intact between the partial unitary components 58 and 60. By placing bone-component and/or component-component transitions in areas of lower load, a smooth surface is ensured along the load line, resulting in less component wear.

Partial unibody components may include a variety of internal geometries in accordance with the present invention. FIG. 8 shows a PFJ/medial condyle component 64 with a faceted interior in the anterior to posterior direction comprising flat surfaces 66, 68, 70, 72 and 74. FIG. 9 shows a PFJ/medial condyle component 76 with a curved interior surface 78. FIG. 10 shows a unitary component 80 with a combined curved and flat interior comprising a curved surface 82 and a flat surface 84. Of course, any of the components may be constructed with any of the interior geometries shown herein.

Moreover, the interior surfaces may be constructed with a variety of geometries in the medial to lateral direction. By way of example, but not of limitation, FIG. 11A shows a flat interior 86 taken across line A-A of FIG. 8, 9 or 10. FIG. 11B shows a curved interior 88 while FIG. 11C shows a faceted interior 90. FIG. 11D shows interior 92 with curved sides and a flat bottom while FIG. 11E shows an interior 94 with flat sides and a curved bottom. These shapes accommodate local bone geometry better than previous known shapes and enable the surgeon to leave more healthy bone in the joint regardless of whether the component is to be press-fit or cemented to the healthy bone.

Modified Individual Component

Figures 12, 13:
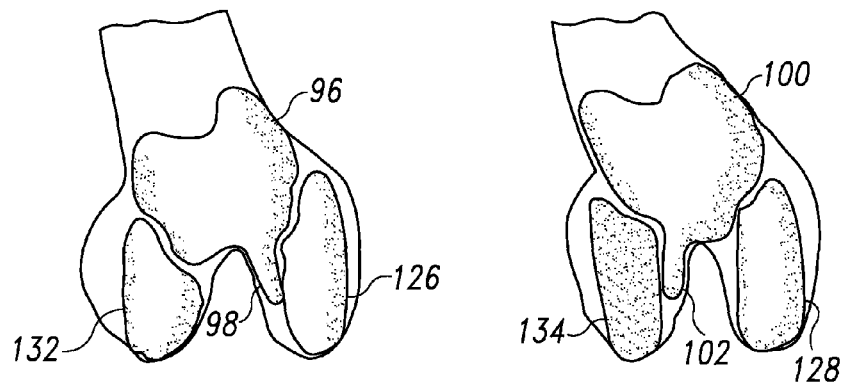
FIG. 12 depicts a PFJ component with a lateral trochlear extension that may be used in a system of the present invention.
FIG. 13 depicts a PFJ component with a medial trochlear extension that may be used in a system of the present invention.
Figure 14:
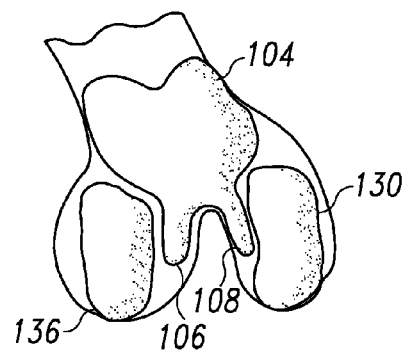
FIG. 14 depicts a PFJ component with a medial trochlear extension and a lateral trochlear extension that may be used in a system of the present invention.

FIG. 12 depicts an alternative embodiment of a PFJ component 96 having a lateral trochlear extension area 98 while FIG. 13 depicts an alternative embodiment of a PFJ component 100 having a medial trochlear extension area 102. FIG. 14 shows a PFJ component 104 having both a medial trochlear extension area 106 and a lateral trochlear extension area 108.

Figures 15A, 15B, 15C:
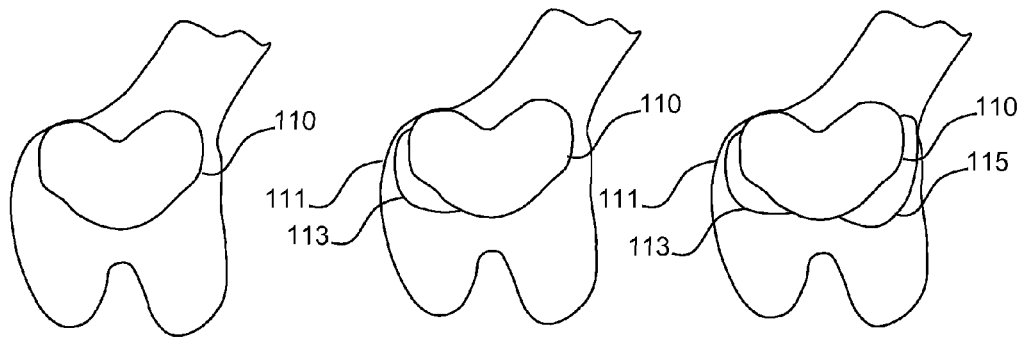
FIGS. 15A, 16 and 17 depict PFJ components with a lateral trochlear extension and a medial trochlear extension for use with femurs of varying widths in accordance with features of the present invention.
FIGS. 15B and 15C depict the PFJ component of FIG. 15A with one and two shims, respectively, to allow the use of the PFJ component of FIG. 15A in patellofemoral areas that are wider than the PFJ component of FIG. 15A.
Figures 16, 17:
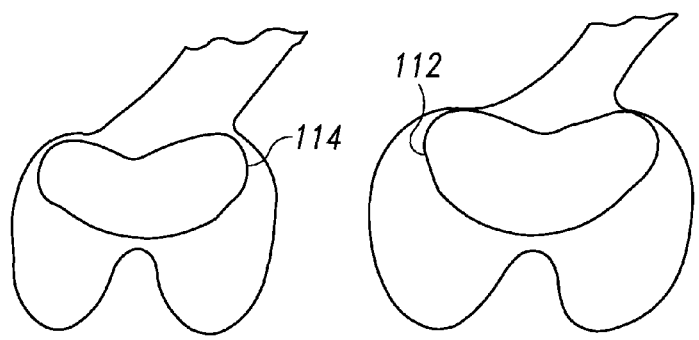

PFJ components may be provided in varying widths for a given anterior to posterior length. By way of non-limiting example, FIGS. 15A, 16 and 17 are intended to provide relative size comparison. As shown in FIGS. 15A, 16 and 17, a PFJ component may be narrow, (PFJ component 110), wide (PFJ component 112), or somewhere in between (PFJ component 114).

Additionally, a PFJ component may be adapted for use in a PFJ area that is wider that would normally be serviceable with a particular PFJ component. Specifically, FIG. 15B shows the PFJ component 110 implanted on a femur 111. The width of the diseased portion of the femur, however, was greater than the width of the PFJ component 110. In every other respect, however, the PFJ component 110 fits the anatomy of the patient very closely. Accordingly, rather than using a larger PFJ component and introducing undesired variances between the implant and the natural bone, a shim 113 was used to replace the portion of the surface of the femur 111 adjacent to the PFJ component 110.

Moreover, in the event the surface area of the femur 111 to be removed is larger than the width of a replacement PFJ component on both the medial and lateral sides, a second shim may be used. Thus, as shown in FIG. 15C, the PFJ component 110 and the shim 111 are augmented with a second shim 115.

Accordingly, one or more shims may be used to fit a narrow PFJ component onto a wider PFJ area. This is particularly beneficial when a PFJ component has the desired anterior/posterior dimensions, but is too narrow for the particular replacement. As discussed in further detail below, the shims may be rigidly or flexibly connected to a PFJ or other component either prior to implanting the component or after implantation. Thus, in one embodiment, a component is provided preconfigured with at least one shim that may be trimmed to fit a particular patient. In alternative embodiments, the shim is spaced apart from the component such as by using spacer beads (see FIG. 35B).

Figure 15D:
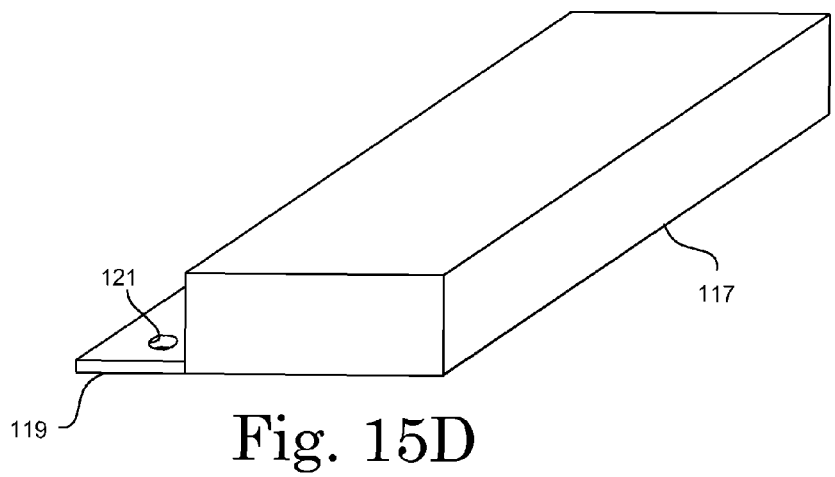
FIG. 15D depicts a shim with a flap for attachment to a bone and/or attachment underneath an adjacent component that may be trimmed as needed to be used with the PFJ component of 15A.

In one embodiment shown in FIG. 15D, a single sized shim 117 is provided with a flap 119. The flap 119 is configured to be placed underneath an adjoining component. The flap 119 includes a hole 121 to facilitate connection to a bone. The flap 119 may thus be attached directly to the bone using a tack through the hole 121 or using bone cement. The adjoining component is then implanted on top of the flap 119. In this embodiment, the shim 117 is flexible and oversized. That is, the shim 117 is wider than would be required in most situations. Accordingly, once the actual dimensions of the area for which a shim is to be used is determined, the shim 117 is resected to the desired dimensions.

Figures 15E, 15F, 15G:
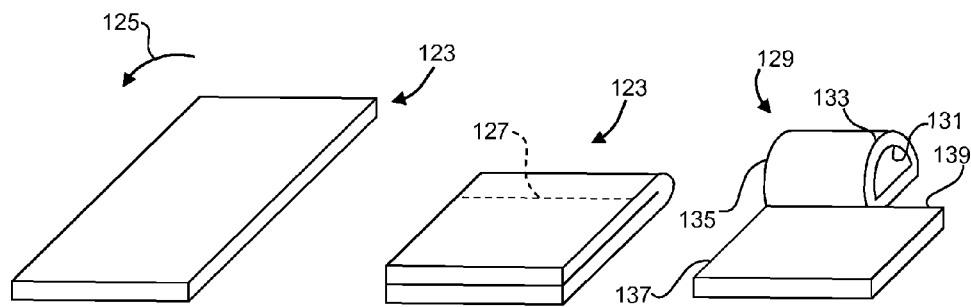
FIG. 15E depicts a shim sheet that may be folded or trimmed to provide the desired dimensions for a shim.
FIG. 15F depicts the shim sheet of FIG. 15E folded to provide additional width.
FIG. 15G depicts a shim with a flap for attachment to a bone and/or attachment underneath an adjacent component and a pocket that may be filled and trimmed as needed to be used with the PFJ component of 15A along with an extension that may be used to seal the pocket.

Another embodiment of a shim is shown in FIG. 15E. The shim 123 is a sheet of material that may be formed to the desired dimensions. For example, the shim 123 may be folded in the direction of the arrow 125 to provide the configuration shown in FIG. 15F. The shim 123 in FIG. 15F is folded in half so as to double the width of the shim 123 when the shim 123 is implanted. The shim 123 may be folded more than once to provide additional width. Additionally, the shim 123 may be folded lengthwise, crosswise, or in any other desired manner. The shim 123 may further be cut, such as along the dashed line 127 to the desired height.

In yet a further embodiment, a shim 129 shown in FIG. 15G is provided with a pocket 131. The pocket 131 includes an open end 133 and a closed end 135. The shim 129 further includes a flap 137 and an extension 139. A desired amount of material such as bone chips, biologic material or some other biocompatible material may be placed in the pocket 131 to provide a shim of the desired size. The pocket 131 may be sealed prior to implantation or during implantation, such as by insertion of tack through the end 133. The flap 137 may also be used to tack the shim 129 into place or the flap 137 may be placed underneath an adjacent component. Alternatively, the flap 137 may be rolled over the top of the pocket 131 and the extension 139 may be used to seal the pocket 131.

A shim may be made from a variety of materials. By way of example, shims may be made from biologically active, inactive or passive materials including fabrics, bone chips and flexible materials. Additionally, in the event some gap remains, filler material such as bone wax, cement, polyurethane or other flexible or biological material may be used to fill the gap.

Figures 18, 19, 20:
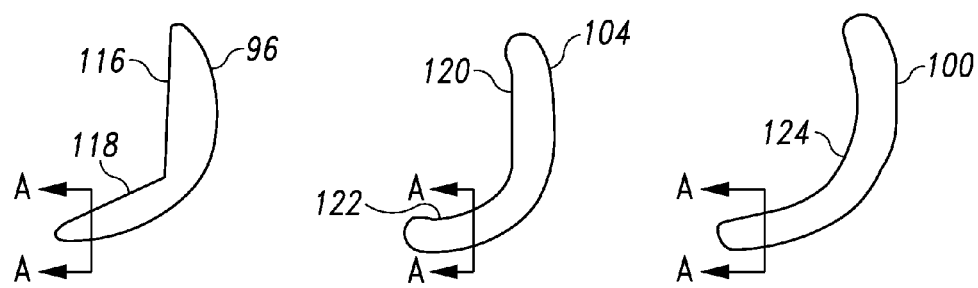
FIG. 18 depicts a faceted interior in the anterior to posterior direction of a patellar femoral component that may be used in a system of the present invention.
FIG. 19 depicts a combined flat and curved interior in the anterior to posterior direction of a patellar femoral component that may be used in a system of the present invention.
FIG. 20 depicts a curved interior in the anterior to posterior direction of a patellar femoral component that may be used in a system of the present invention.

Returning to the discussion of PFJ components, the PFJ components may include a variety of internal geometries in accordance with the present invention. FIG. 18 shows the PFJ component 96 of FIG. 12 with a faceted interior in the anterior to posterior direction comprising a flat surface 116 and a flat surface 118. FIG. 19 shows the PFJ component 104 of FIG. 14 with a combined curved and flat interior comprising a flat surface 120 and a curved surface 122. FIG. 20 shows the PFJ component 100 of FIG. 13 with a curved interior 124. Of course, any of the PFJ components may be constructed with any of the interior geometries shown herein.

Figure 21:
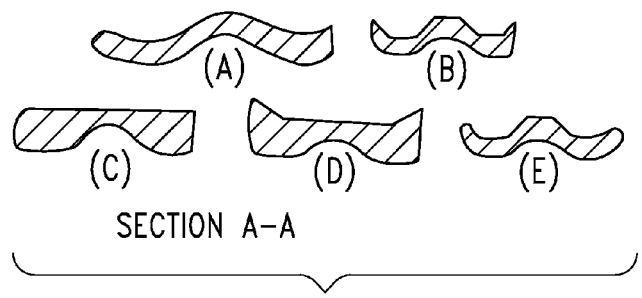
FIG. 21 depicts various cross-sections in the medial to lateral direction that may be used in the anterior portions of the components of FIGS. 18, 19 and 20.

The cross-section of these components in the medial-lateral direction may also be formed in a variety of shapes, such as cross-sections (a), (b), (c), (d) and (e) shown in FIG. 21. As shown in these figures, the cross-section taken along line A-A of FIGS. 18, 19 or 20 may comprise flat areas, curved areas, and combinations of flat and curved areas.

Unicondylar Components

Similarly, unicondylar components, such as lateral condyle components 126, 128, and 130 and medial condyle components 132, 134, and 136 of FIGS. 12, 13 and 14, may contain various internal geometries, as shown in FIGS. 22, 23 and 24. FIG. 22 shows the medial condyle component 132 with a faceted interior in the anterior to posterior direction comprising a flat surface 138, a flat surface 140 and a flat surface 142. FIG. 23 shows the medial condyle component 136 with a curved interior 144 in the anterior to posterior direction and FIG. 24 shows the lateral condyle component 126 with a combined curved and flat interior comprising a flat surface 146 and a curved surface 148 in the anterior to posterior direction.

Moreover, the unicondylar components may be configured to provide for extended flexion. Extended flexion is provided by the extended posterior portion 150 of the condyle component 152 shown in FIG. 25. The extended portion provides additional surface area for contact with a tibia as the tibia is rotated about the femur. Of course, any of the condyle components may be constructed with any of the interior geometries shown herein. Moreover, extended flexion may similarly be provided in unibody construction by extension of the condylar area.

The cross-section of the condyle components in the medial-lateral direction may also be formed in a variety of shapes, such as those shown in FIGS. 26A, 26B, 26C, 26D and 26E. As shown in these figures, the cross-section taken along line A-A of FIGS. 22, 23 and 24 may comprise flat areas, curved areas, and combinations of flat and curved areas. More specifically, FIG. 26A shows a flat interior 154. FIG. 26B shows a curved interior 156 while FIG. 26C shows a faceted interior 158. FIG. 26D shows an interior 160 with curved sides and a flat bottom while FIG. 26E shows an interior 162 with flat sides and a curved bottom. Combinations of curved and flat geometries are not limited to these figures. Moreover, these internal geometries may be used with all implant components disclosed herein and are not limited to unicondylar components.

Augments

To further facilitate accommodation of local bone geometry, augments may be placed between a component and a portion of resected bone. The use of augments further provides for reconstruction of a knee that more closely resembles the natural knee without the need for a large number of PFJ and/or condylar components as the augments may be configured to effectively enlarge the outer boundary of the PFJ and/or condylar components. Thus, as shown in FIGS. 27, 28 and 29, augments 164, 166, 168, 170, 172 and 174 may be placed between an implant component and a bone, thus moving the implant components farther away from the bone.

The outer surface of an augment is shaped to conform to the interior surface of the component. For example, the exteriors of augment 164 and augment 166 are faceted in the anterior to posterior direction to fit within the faceted interior of component 176. Augments 168 and 170 are curved to fit within the interior curve of component 178. Augment 172 is flat to fit against the flat portion of the inner surface of component 180, while augment 174 is curved to fit against the curved inner portion of component 180.

Of course, the inner portion of the cross-section of the augments in the medial to lateral direction may be shaped similarly to the inner portion of the condyle components discussed above. Thus, a variety of cross-sectional shapes may be realized by various combinations of faceted, curved and straight inner contours with faceted, straight and curved outer contours.

By way of example, but not of limitation, FIG. 30A shows an augment 182 with a faceted inner surface 184 as well as a faceted outer surface 186. The augment 182 of FIG. 30A may be used with a component having the cross-section shown in FIG. 26C. The augment 188 shown in FIG. 30B may also be used with a component having the cross-section shown in FIG. 26C. However, instead of a faceted inner surface, the inner surface 190 of augment 188 is curved. The augments 192, 194 and 196 of FIGS. 30C, 30D and 30E may be used with a component having the cross-section shown in FIG. 26E, so as to realize an inner surface that is faceted (inner surface 198 of augment 192), flat (inner surface 200 of augment 194), or curved (inner surface 202 of augment 196).

Joining and Fitting Mechanisms

Figure 31A:
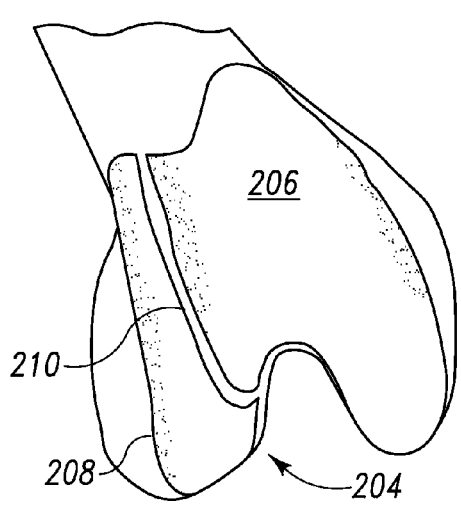
FIG. 31A depicts a split anterior configuration of a tibial femoral and a PFJ component that may be used in a system of the present invention.
Figure 32B:
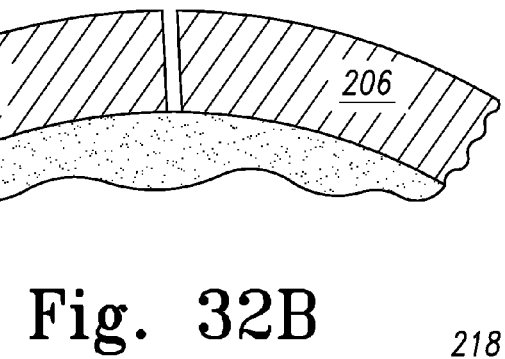
FIG. 32B depicts a partial cross-section of the components of FIG. 31B.
Figure 32A:
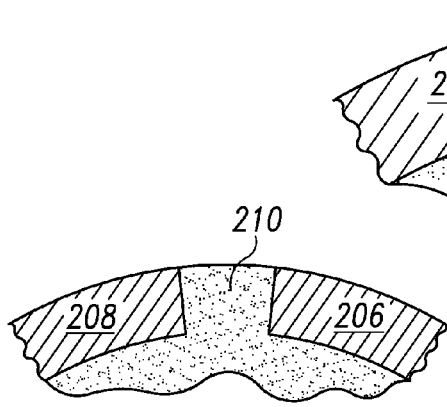
FIG. 32A depicts a partial cross-section of the components of FIG. 31A about a bone tide.

FIG. 31A shows yet another embodiment of a femoral replacement component 204 that comprises a combined PFJ and lateral condyle area 206, and a medial condyle area 208. Alternatively, a component 204 may include an upper condyle area and a lower condyle area. As shown in FIG. 31A, component pieces 206 and 208 may be implanted about a bone tide 210. A close-up of the junction between component pieces 206, 208, and bone tide 210 is shown in FIG. 32A. Bone tide 210 may be comprised of bone, cartilage or a synthetic material.

Figure 31B:
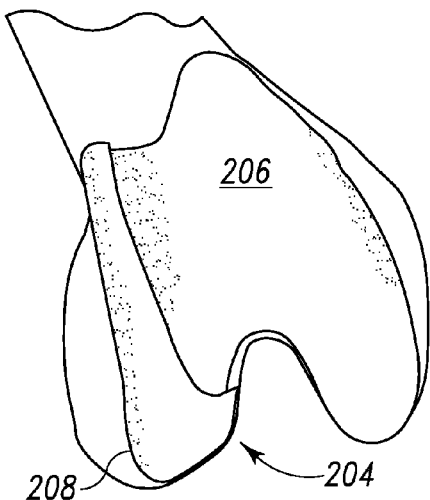
FIG. 31B depicts the complimentary tibial femoral component and the PFJ component of FIG. 31A implanted so as to abut one another without coupling of the components.

In this embodiment, the component pieces 206 and 208 are configured to be complimentary. Thus, if desired, a surgeon may implant the component pieces 206 and 208 without a bone tide. Thus, as is depicted in FIG. 31B, the components 206 and 208 are abutted and as depicted in FIG. 32B, the components 206 and 208 are not coupled.

Figure 33:
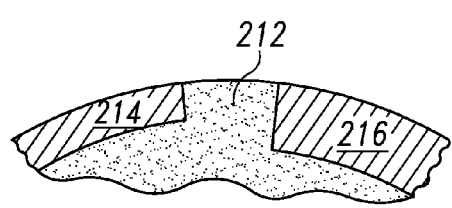
FIG. 33 depicts an alternative partial cross-section of components having different thicknesses about a bone tide that may be used in a system of the present invention.
Figure 34:
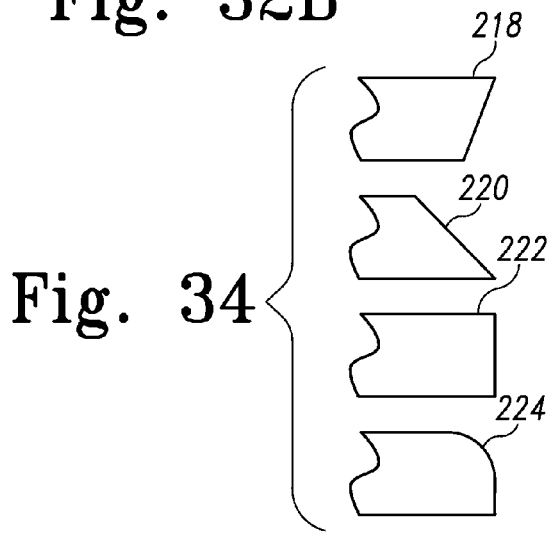
FIG. 34 depicts alternative edge configurations of implants that may be used in a system of the present invention.

With reference to FIG. 33, an alternative embodiment of a bone tide junction is shown. In this embodiment, bone tide 212 is located between component pieces 214 and 216. Component pieces 214 and 216 have different depths. According to a further embodiment, component pieces may be formed with ends of a variety of shapes. Thus, as shown in FIG. 34, component piece 218 is angled inwardly from the upper surface of the component piece 218, component piece 220 is angled outwardly from the upper surface of the component piece 220, component piece 222 has a square end, and component piece 224 is radiused.

The radiused end of a component piece may include a plurality of segments of different radii of curvature, with a first segment having a radius of curvature larger than a second segment, the second segment located between the first segment and the side of the component. Such a configuration is useful in reducing friction along a load line that passes over the junction of adjacent components. The slight curvature of the edges ensures that an object traveling along the load line does not encounter a ridge resulting from a misalignment of the components when passing from one component to the adjacent component.

Components made in accordance with the principles of the present invention may be inset into resected bone or a bone tide. To enhance the retention of the components in the resected area, bead spacers may be formed in the sides of components. As shown in FIG. 35A, component 226 includes bead spacers 228 and 230. Similarly, component 232 includes bead spacers 234 and 236. To use bead spacers in a cementless application, a rescission is made in the bone that comports with the size of the replacement component without the bead spacers. Thus, when the component is inserted into the resected area, the bead spacers are forced tightly against the bone in the wall of the rescission. Bead spacers may be in the form of a single bead, a partial ridge about the component, or a continuous ridge. Those of ordinary skill in the art will appreciate that alternative materials may be used to maintain the components in the desired location in place of or in addition to bead spacers including, but not limited to, porous coatings, orthobiologic materials, lacey membranes, grouting, and cement.

Moreover, the spacer beads may be used when two components are to be implanted side by side. FIG. 35B shows component 221 with bead spacer 223. Similarly, component 225 includes bead spacer 227. In this embodiment, both of the components include bead spacers. In such embodiments, it is preferred to arrange the bead spacers so that they do not interfere with bead spacers on an adjacent component as this would increase the minimum distance between the adjacent components. In the event that there is relative motion between the components 221 and 225, the edges of the components 221 and 225 will not rub against each other since the spacers 223 and 227 maintain a minimum separation between the components 221 and 225.

Of course, the bead spacers 223 and 227 may contact the adjacent component 225 or 221, respectively. Thus, in certain embodiments it is desirable to either make the bead spacers 223 and 227 from a resilient material or to coat the bead spacers 223 and 227 with a resilient material. Moreover, the gap between the components that is maintained by the bead spacers 223 and 227 may be filled with a bone wax, cement, polyurethane or other flexible or biologic material to provide additional stability while reducing wear products.

A number of alternative embodiments of spacers and spacer configurations are contemplated within the scope of the invention. By way of example, in one embodiment, only one component includes bead spacers. In such an embodiment, the bead spacer may be formed with the component or may be attached to the component at a later step.

In a further embodiment, the spacer is not attached to either component. By way of example, FIG. 35C shows a spacer device 229 that includes a number of spacers 231 on a substrate 233. The substrate 233 includes a number of attachment holes 235 and flaps 237 and 239. The attachment holes 235 may be used to tack the spacer device to a bone. The flaps 237 and 239 are configured to be placed underneath adjacent replacement components. Thus, the spacers 231 are between the adjacent sides of the adjacent components. In this embodiment, the substrate 233 is made of a flexible material. This allows the spacer device 231 to be positioned along a curved component. Moreover, the spacer device 231 may be cut so as to only provide a limited number of spacers 231. Thus, the spacer device 231 may be individualized for a particular implant scenario.

Of course, the spacers need not be in the shape of a bead, box or other symmetrical shape. Spacer shim 233 shown in FIG. 35D is generally wedge shaped. Thus, the shim 233 may be wedged between the patellofemoral component 235 and the condylar component 237 to provide additional stability to the replacement components as well as ensuring that the patellofemoral component 235 and the condylar component 237 do not come into direct contact with one another. It is contemplated that in certain embodiments, the shim 233 may be cut during the operation to the desired length. Accordingly, the shim 233 may be cut along the line 239 to minimize bone resection.

The use of shims of various shapes, such as the wedge shape of shim 233, allows for the same replacement components to be used in a range of patient geometries. By way of example, FIG. 35E depicts a femur with a condyle 241 that is turned inwardly as compared with the condyle 243 of FIG. 35D. By simply inserting the shim 233 further between the adjacent patellofemoral component 235 and the condylar component 237, the same patellofemoral component 235 and condylar component 237 may be used as shown in FIG. 35E. Thus, the shim 233 allows for different pose of the components. By making the shim in a more complex shape, such providing different tapers along different sides, even greater flexibility may be achieved.

Of course, the various spacing components may also be used in different combinations. By way of example, a shim may include spacer beads along its sides. Moreover, additional spacers may be provided on the components or spacers may be provided that are attached to the components as needed. Thus, a significant increase is realized in the ability to use a limited number of components in a wide range of patient geometries.

The spacers may be made from a variety of materials. By way of example, spacers may be made from biologically active, inactive or passive materials including fabrics, bone chips and flexible materials. Additionally, in the event a spacer does not completely fill the area between adjacent components or between a component and the adjacent bone, filler material such as bone wax, cement, polyurethane or other flexible or biological material may be used to fill the gap.

Figure 36:
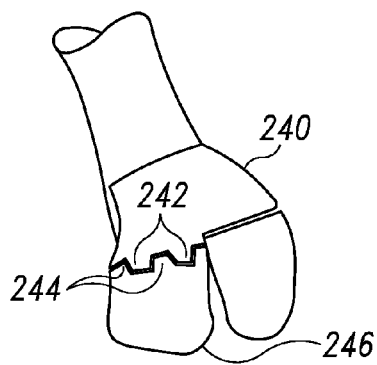
FIG. 36 depicts a key structure that may be used at the interface between components in a system of the present invention.

Implantation of components may also be enhanced by coupling components to one another. To enhance the press fitting between components, a component may be formed with a key that mates with an inverse key of another component. By way of example, as shown in FIG. 36, the component 240 includes a key 242 that mates with the key 244 of the component 246 along the entire junction of the components 240 and 246.

Figure 37:
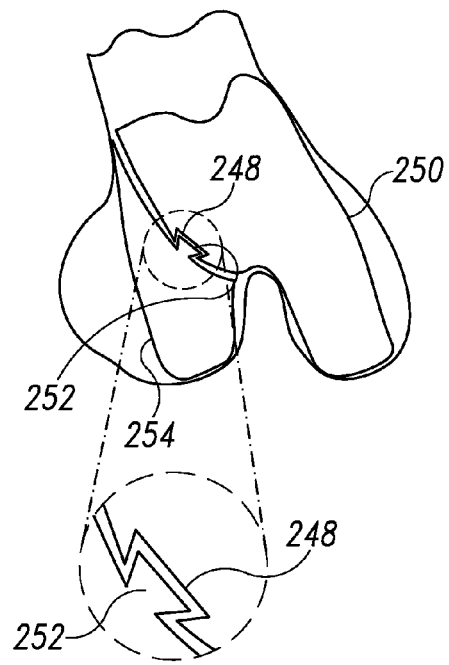
FIG. 37 depicts an alternative key structure that may be used at the interface between components in a system of the present invention.
Figure 38:
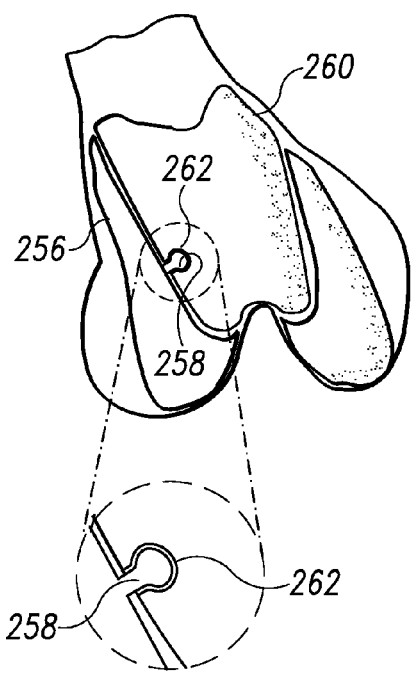
FIG. 38 depicts an alternative key structure that may be used at the interface between components in a system of the present invention.

Alternatively, a single key may be used to engage components together as shown in FIG. 37 wherein the key 248 of the component 250 mates with the key 252 of the component 254. An alternative form of the single key is shown in FIG. 38 where component 256 has an extending button 258 and the component 260 has button receptacle 262 to receive the button 258. Keys may thus comprise a single mating element or may comprise a plurality of mating elements. Moreover, use of different types of keys in conjunction with each other may be desired when fitting components. These alternative embodiments are within the scope of the present invention.

Figure 39:
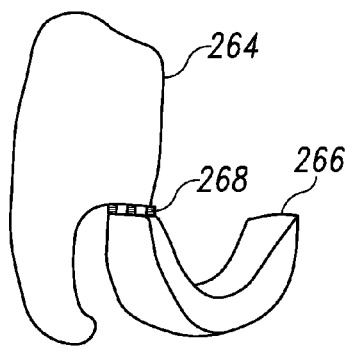
FIG. 39 depicts a hinge that may be used at the interface between components in a system of the present invention.

In another alternative embodiment, a hinge may be formed between components to support movement without component separation. As shown in FIG. 39, the component 264 is joined to the component 266 by a hinge 268. The hinge 268 may be a traditional mechanical hinge. Alternatively, the hinge 268 may be made from a synthetic material that is deigned to yield under force. The use of two components joined by a hinge as opposed to a single component or firmly joined components reduces the chance of a fracture. For example, if the components 264 and 266 are formed as a single rigid component, and if one end of the rigid component is firmly set in bone or cement and a second end of the rigid component is not fully underlain with cement, or if the bone under the second end of the rigid component is compressed, the rigid component will flex at a location between the first and second end. Such flexing or working of the rigid component leads to a stiffening of the material in the rigid component which may result in brittle fracture. However, when joined in the manner shown in FIG. 39, the hinge 268 allows for flexure or movement between the two components 264 and 266 without working any material.

Figure 40:
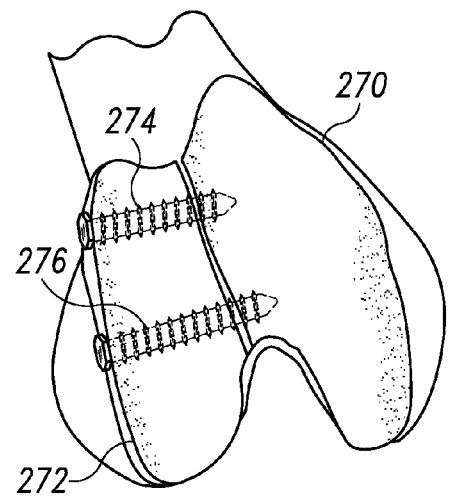
FIG. 40 depicts one embodiment of two knee components coupled together with screws at the anterior of a femur that may be used in a system of the present invention.
Figure 41:
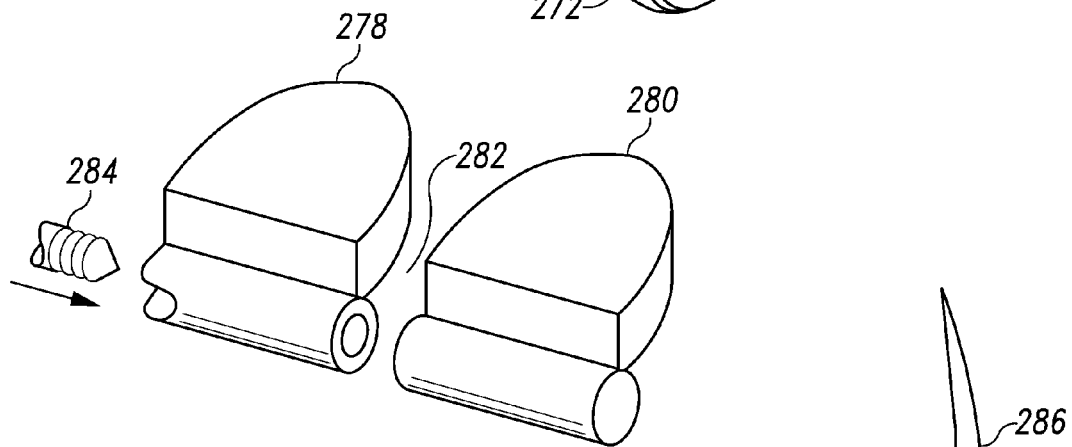
FIG. 41 depicts components connected together by a screw with space, bone or spacer material between the components that may be used in a system of the present invention.

Femoral, patellar and/or tibial components may also be connected one to another by mechanical means, such as screws. Thus, FIG. 40 shows a component 270 joined to a component 272 by screws 274 and 276. The components may be, but need not be, abutted to be joined. With reference to FIG. 41, the components 278 and 280 are shown separated by a space generally indicated as the space 282. A screw 284 may be used to connect the component 278 to the component 280 while maintaining the space 282 between the component 278 and the component 280.

Figure 42:
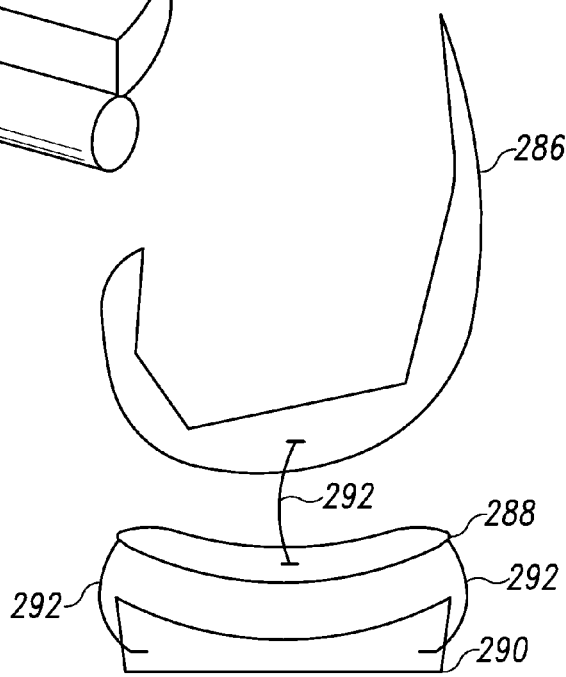
FIG. 42 depicts components and spacer material connected together without a screw, with the spacer material between the component that may be used in a system of the present inventions.

Furthermore, the connection of components may be made either on the same bone or alternatively across the joint space between bones. By way of example, FIG. 42 depicts PFJ/condyle component 286 connected to spacer 288, which is in turn connected to tibial component 290. Connection is made by connectors 292. The connectors between components may be bone, artificial tissues and/or grafts.

Figure 43:
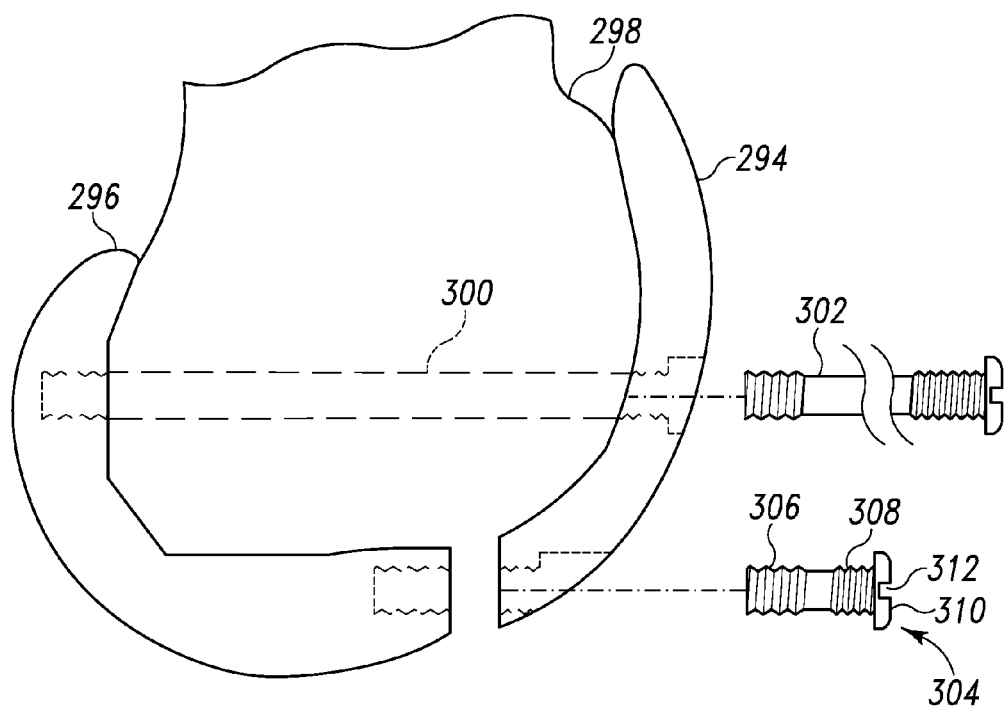
FIG. 43 depicts a threaded screw coupling of components that may be used in a system of the present invention in which one or more of the screws have different thread pitches.

The screws may also pass through bores in a bone to hold component sides opposed to one another through the bone. With reference to FIG. 43, a component 294 and a component 296 are located against a femur 298 which has a bore 300 therethrough. Accordingly, the component 294 and a component 296 may be joined by insertion of a screw 302 through the bore 300 while the screw 304 joins the components 294 and 296 underneath the femur 298. As further shown by screw 304, the screws may be provided with threads 306 and 308 which are different pitches to help control the clamping force. In this embodiment, head 310 of screw 304 includes a receptacle 312 to receive a torque control wrench to facilitate installation of the screw 304.

Figure 44:
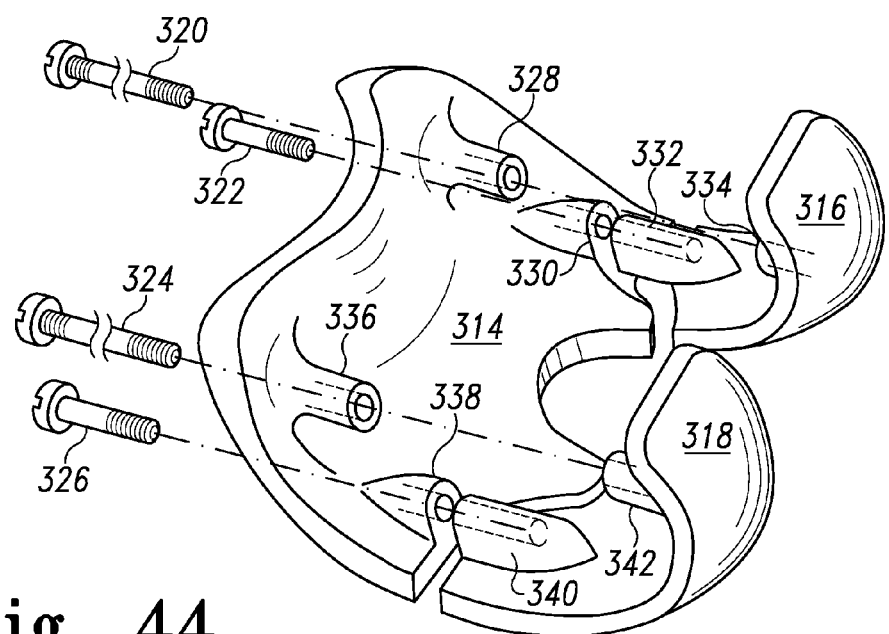
FIG. 44 depicts a component coupling arrangement that uses attachment posts with screws for component coupling that may be used in a system of the present invention.

FIG. 44 shows a femoral component that may be joined by screws in the manner discussed with respect to FIG. 43. A unitary component 314 that includes a PFJ area, a medial condyle, and a lateral condyle may be adjustably joined to the posterior condyles 316 and 318 by screws 320, 322, 324, and 326. Components 314, 316 and 318 are thin implant components that in this embodiment are curved in the anterior/posterior direction as well as the medial/lateral direction. Components that are not so curved are considered to be within the scope of the present invention, as are components with internal geometries which have been discussed above.

Attachment posts 328, 330, 332, 334, 336, 338, 340, and 342 are formed in components 314, 316, and 318 to extend from the interior surfaces of the components. Screws 320, 322, 324, and 326 may be placed through the attachment posts 328, 330, 332, 334, 336, 338, 340, and 342 so the posts provide additional support for coupling of the components without sacrificing a large amount of bone for implanting of the components.

Figure 45:
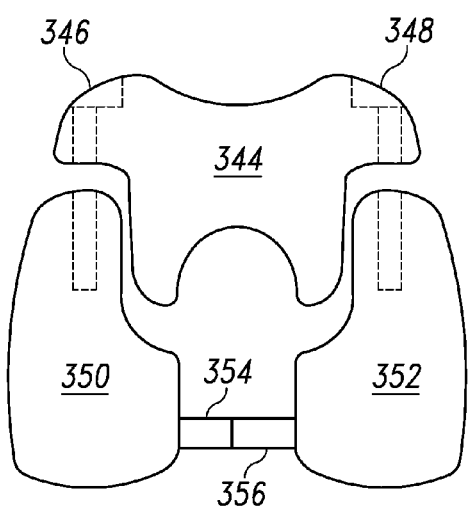
FIG. 45 is a front perspective view of components with an alternative attachment post arrangement for component coupling that may be used in a system of the present invention.
Figure 46:
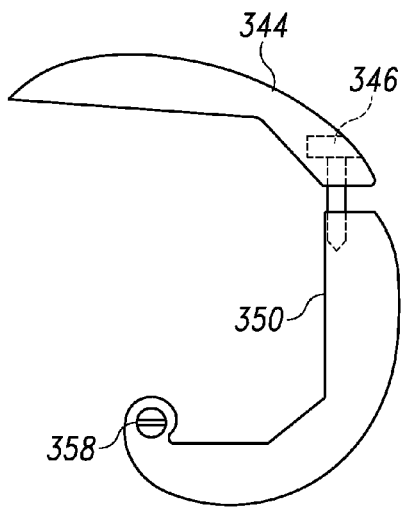
FIG. 46 is a side perspective view of the components of FIG. 45.

An alternative embodiment is shown in FIG. 45 where a PFJ component 344 is coupled by vertically oriented screws 346 and 348 to a medial condyle component 350 and to a lateral condyle component 352. The condylar components 350 and 352 include attachment posts 354 and 356 extending from the components 350 and 352, respectively, in the medial/lateral direction. FIG. 46 is a side view of the components of FIG. 45 showing the PFJ component 344 connected to the medial condyle component 350 by the screw 346. A screw 358 is inserted through the attachment posts 354 and 356 to join the condylar components 350 and 352. Alternatively, the medial condyle component 350 and the lateral condyle component 352 may be formed as a unitary component.

Figure 47:
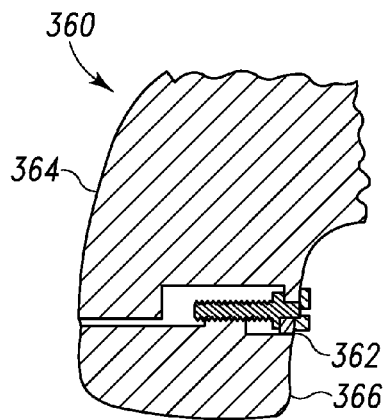
FIG. 47 depicts a single piece component that may be used in a system of the present invention with a screw mechanism used to adjust the relative position of two areas of the component.

Screws may also be used in components to provide a surgeon with the ability to change the position of an implanted component relative to another component. FIG. 47 shows an embodiment including a single piece component 360 with a screw mechanism 362 for lateral/medial adjustments between the PFJ area 364 and the medial condyle area 366. The ability to mechanically modify the relative positions of areas of a component in this manner enables a surgeon to better match the component to the local implantation geometry.

Components may further be resiliently connected. By way of example, the PFJ component 800 may be connected to the condylar components 802 and 804 by the resilient connectors 806 and 808, respectively. The resilient connector 806 engages the connector receptacle 810 on the PFJ component 800 and the connector receptacle 812 on the condylar component 802. Similarly, the resilient connector 808 engages the connector receptacle 814 on the PFJ component 800 and the connector receptacle 816 on the condylar component 804. Suitable resilient materials include nitinol, polyurethanes, elastomers and liquid metals.

Figure 48A:
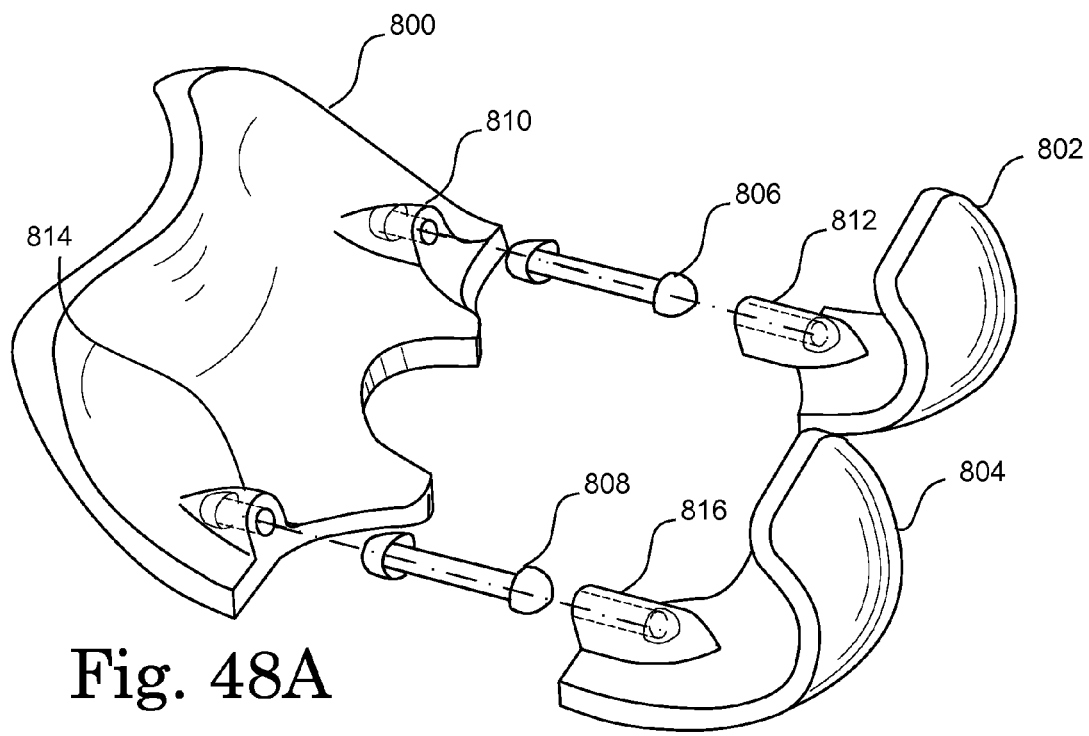
FIG. 48A depicts a component coupling arrangement that uses connector receptacles with resilient connectors for component coupling that may be used in a system of the present invention.
Figure 48B:
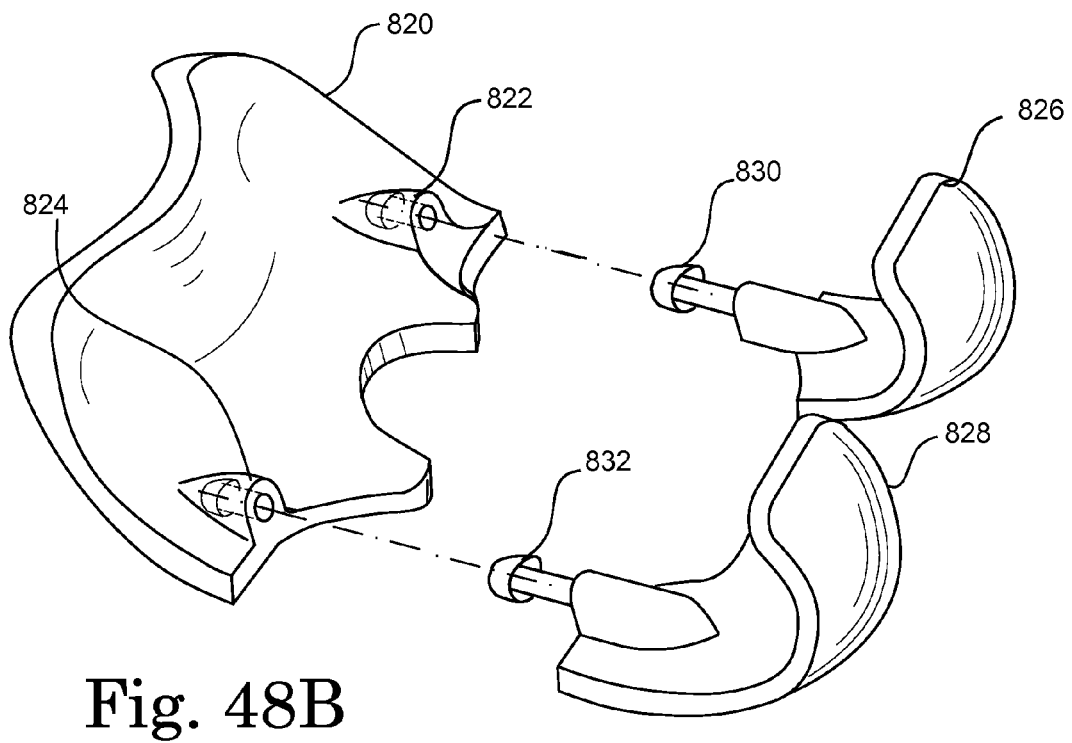
FIG. 48B depicts a component coupling arrangement that uses connector receptacles with resilient connectors integrally formed with one component for component coupling that may be used in a system of the present invention.

In an alternative embodiment, the resilient connectors are integral to one of the components to be connected. With reference to FIG. 48B, the PFJ component 820 is configured much like the PFJ component 800 and includes connector receptacles 822 and 824. The condylar components 826 and 828, however, include resilient connectors 830 and 832, respectively. By providing the condylar components 826 and 828 with the integral resilient connectors 830 and 832, the number of components within a kit is reduced.

Returning to FIG. 48A, the resilient connectors 806 and 808 are symmetrical. That is, either end of either of the resilient connectors 806 and 808 may be inserted into any of the connector receptacles 810, 812, 814 or 816. This is useful in minimizing the number of components that are required in a kit that is used to individualize a prosthetic system for a particular implantation as the same connectors may be used with any of a variety of PFJ components and condylar components.

In certain instances, however, the resilient connectors and connector receptacles may be formed so as to reduce the potential for incorrectly connecting adjacent components. By way of example, in the event a condylar component comprises two subcomponents, the connector receptacles used to connect the two subcomponents may be configured differently from the connector receptacles used to connect the condylar component to a PFJ component. Thus, improper positioning of the condylar subcomponents may be prevented.

Figure 49A:
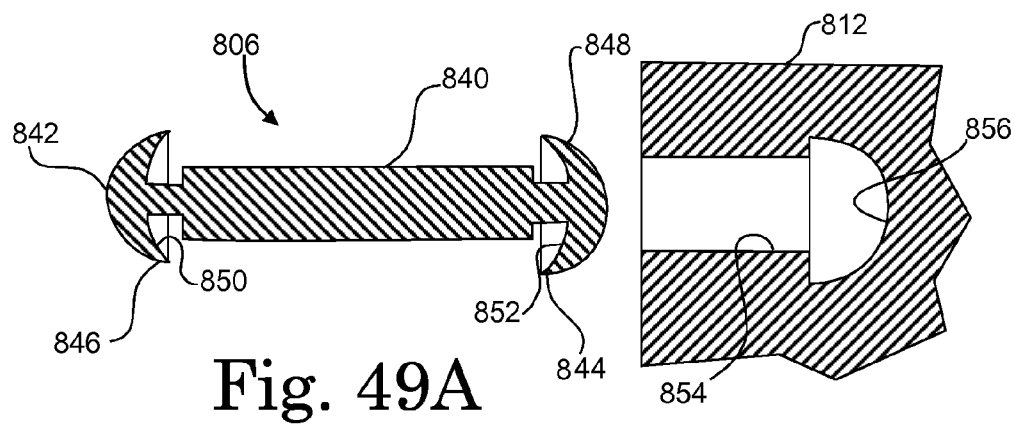
FIG. 49A depicts a cross section of a resilient connector of FIG. 48A.

FIG. 49A depicts a cross-sectional view of the resilient connector 806 positioned to be inserted into the connector receptacle 812. The resilient connector 806 includes a stem portion 840 and two end portions 842 and 844. Each of the end portions 842 and 844 include flared portions 846 and 484, respectively that define cavities 850 and 852. The connector receptacle 812 includes a channel 854 and a chamber 856. The diameter of the channel 854 is slightly larger than the diameter of the stem portion 840 and slightly smaller than the diameter of the flared portion 848. The chamber 856 is slightly larger than the end portion 844.

Accordingly, as the resilient connector 806 is forced into the connector receptacle 812, the cavity 852 allows the flared portion 848 to bend inwardly so as to fit within the channel 854. Once fully inserted, the flared portion 848 is allowed to resiliently return to the condition shown in FIG. 49A, but within the chamber 856. Since the diameter of the flared portion 848 is greater than the diameter of the channel 854, the resilient connector 806 is inhibited from being withdrawn from the connector receptacle 812.

Moreover, further movement of the resilient connector 806 toward the connector receptacle 812 is inhibited since the end portion 844 abuts the chamber 856. Thus, the stem portion 840 of the resilient connector 806 may be used to space apart the PFJ component 800 from the condylar component 802. Such spacing reduces the production of wear debris in the event that there is relative motion between the PFJ component 800 and the condylar component 802 after implantation.

Figure 49B:
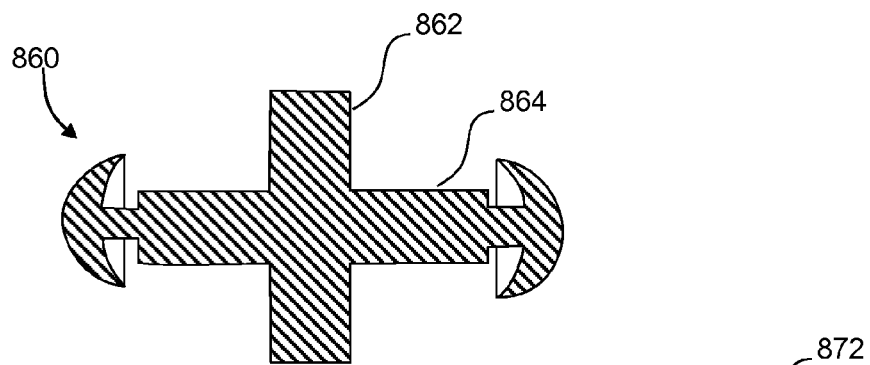
FIG. 49B depicts an alternative connector with an integrally formed spacer that may be used in a system of the present invention.

In an alternative embodiment shown in FIG. 49B, a resilient connector 860 includes a spacer 862 integrally formed into the stem portion 864 of the resilient connector. Alternatively, the components may be coated with a resilient material so as to minimize the production of wear products. When coating the components, it is only necessary to coat the portions of the components that may rub against adjacent components. Of course, only one of the adjacent components need be coated in order to provide the desired reduction in wear debris.

Figure 49C:
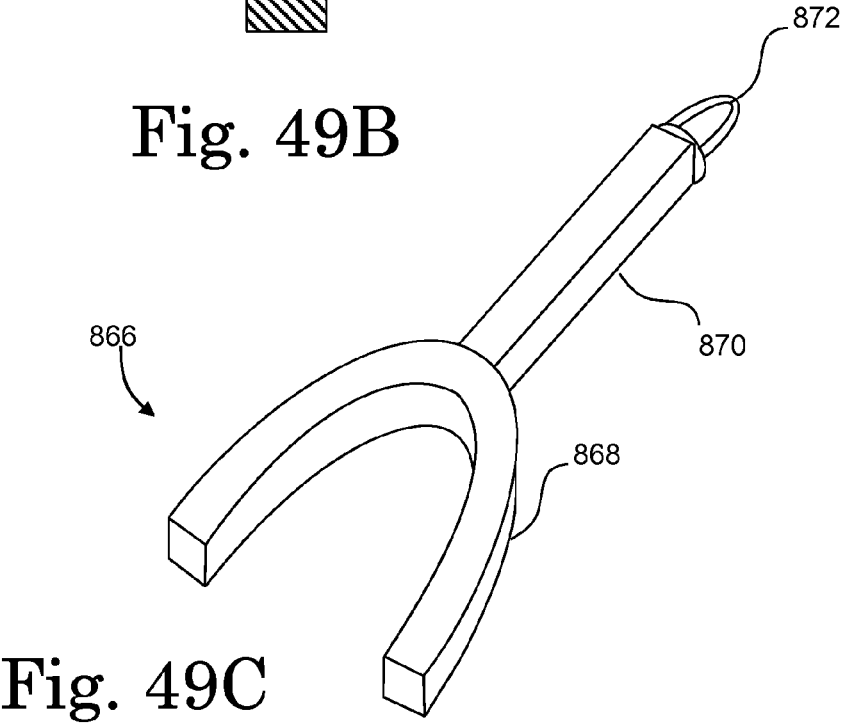
FIG. 49C depicts a temporary or permanent spacer that may be used with the resilient connector of FIG. 49A.

In yet a further embodiment, a separate spacer 866 shown in FIG. 49C may be used with the resilient connector 806. The spacer 866 includes a bridging portion 868 and a stem portion 870 with a bracket 872. The bridging portion 868 is configured to straddle the stem portion 840 of the resilient connector 806. The stem portion 870 is used to manipulate the spacer 866 into position and the bracket 872 is used to attach a lanyard to the spacer 866 to ensure the spacer 866 is easily located in the event that it becomes dislodged in situ. The spacer 866 may be used to temporarily provide a desired spacing of components as the gap between the components is filled. Alternatively, the spacer 866 may remain in position. In such an application, the stem 870 is cut after the gap between the components is filled and the stem 870 is then removed.

Tibial and Patellar Components

Figure 50A:
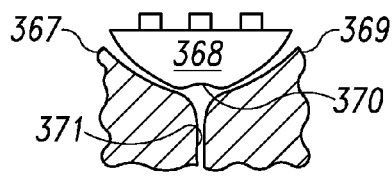
FIG. 50A depicts a patella component above a gap between implanted components that may be used in a system of the present invention with a notch for facilitating patella movement.

Referring now to FIG. 50A, a patellar component 368 is shown above two implanted femoral components 367 and 369. The patellar component 368 includes a notch 370 that accommodates split anterior designs such as the one shown in FIG. 40. Notch 370 reduces impingement of the patella on the junction of a femoral implant. Alternatively, a flat region may be used instead of the notch 370 to reduce impingement on the junction of a femoral implant.

Moreover, the slight curvature at the upper edges of the femoral components 367 and 369 reduce potential friction that may result from even slight misalignment of the femoral components 367 and 369. Similarly, the femoral components 367 and 369 are designed to be implanted with a slight gap 371 between the components along the adjacent edges of the femoral components 367 and 369. The gap 371 reduces the potential for frictional contact between the femoral components 367 and 369 in the event of relative motion between the two components. However, as is apparent from FIG. 50A, the gap 371 is designed to be small enough so that another bone passing over the gap, in this embodiment the patellar component 368 passes freely over the gap 371.

Figure 50B:
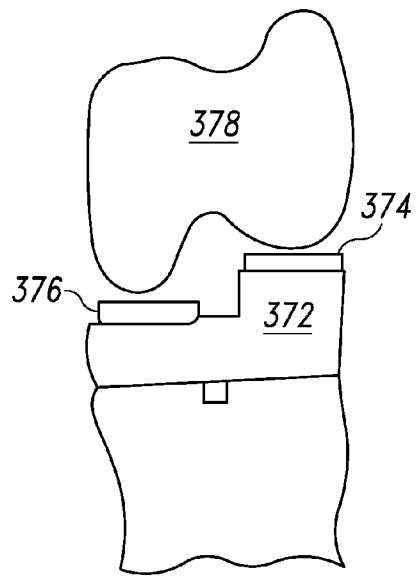
FIG. 50B depicts stepped tibial components that may be used in a system of the present invention.
Figure 50C:
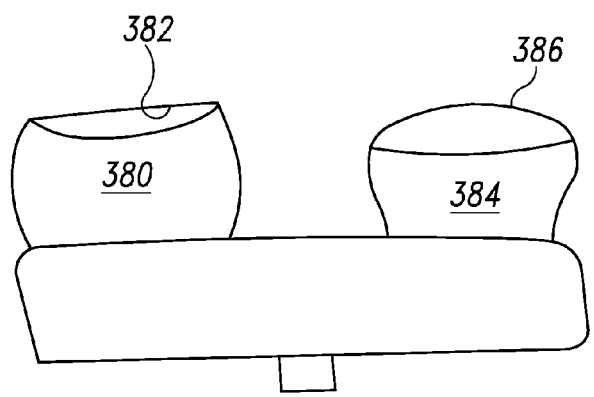
FIG. 50C depicts a tibial component with a convex meniscus and a concave meniscus that may be used in a system of the present invention.

An embodiment of a tibial component is shown in FIG. 50B. Tibial component 372 is stepped to provide a higher support platform for the lateral meniscus 374 than for the medial meniscus 376. This configuration accommodates the asymmetrical condyles of component 378. As shown in FIG. 50C, a medial meniscus 380 may be formed with a concave surface 382 while the lateral meniscus 384 may be formed with a convex surface 386. Such a configuration of meniscus components better conform to normal knee anatomy.

Stepped Components

Figures 51, 52:
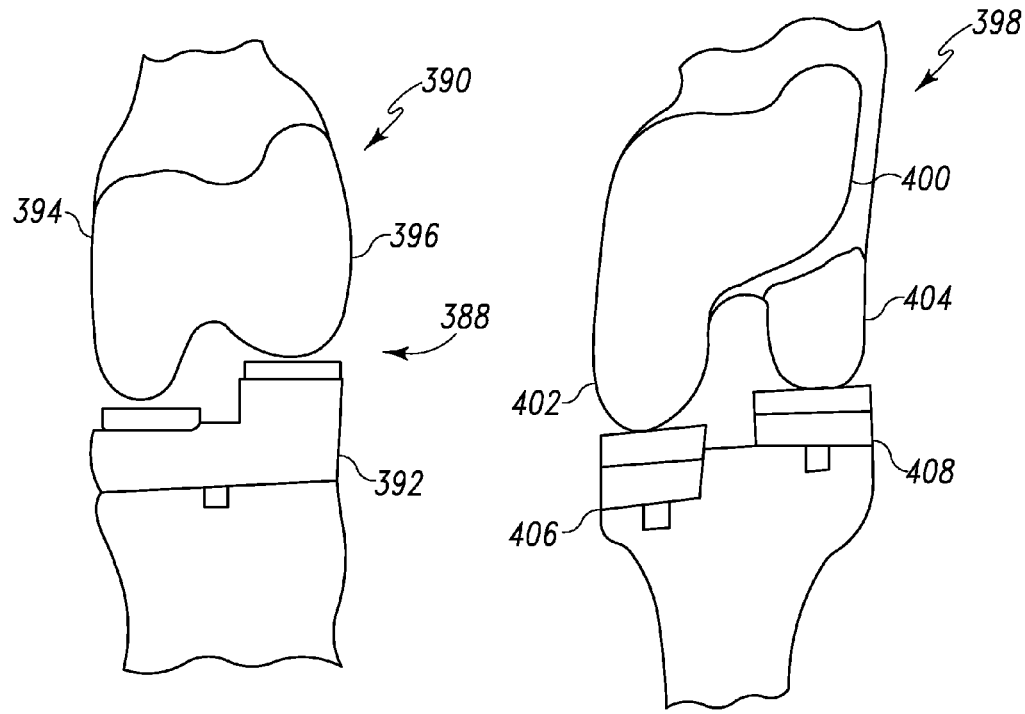
FIG. 51 depicts femoral and tibial components of a total knee replacement with stepped condyle areas that may be used in a system of the present invention.
FIG. 52 depicts a stepped unitary PFJ/condyle component with an additional condylar component that may be used in a system of the present invention.

In addition to the various geometries and configurations discussed above, the present invention provides components for a variety of irregularly shaped bone geometries. FIG. 51 depicts a total knee system 388 with stepped femoral component 390 and stepped tibial component 392. The medial side 394 of the femoral component 390 is more distal than the lateral side 396.

Similarly, FIG. 52 depicts a PFJ/condyle component 398 including a PFJ area 400 and a condyle area 402. PFJ/condyle component 398 in this embodiment is stepped. In accordance with the present invention, even when PFJ/condyle component 398 is implanted, additional components may easily be added at later times. By way of example, FIG. 52 shows a stepped condyle component 404 that may be implanted at a later (or earlier) date than PFJ/condyle component 398. Moreover, the condyle area 402 of the PFJ/condyle component 398 and the condyle component 404 may be of different sizes. Also, as discussed below, the PFJ/condyle component 398 and the condyle component 404 may have different radii of curvature.

The present invention further provides latitude in optimizing the tibial components for specific patient conditions such as irregular bone geometries for earlier or later implanted components. As shown in FIG. 52, the tibial component inserts 406 and 408 may be implanted at any time before or after the implantation of the femoral components 400 and 404. The tibial component inserts 406 and 408 may advantageously be fixed or meniscal bearing implants. The present invention further provides for individual optimization of the size of the tibial component inserts 406 and 408, irrespective of the size of the other insert or of the femoral components. This allows a surgeon to optimize conformity between the femoral and tibial components while reducing inventory costs.

Condylar Variations

Figures 53, 54:
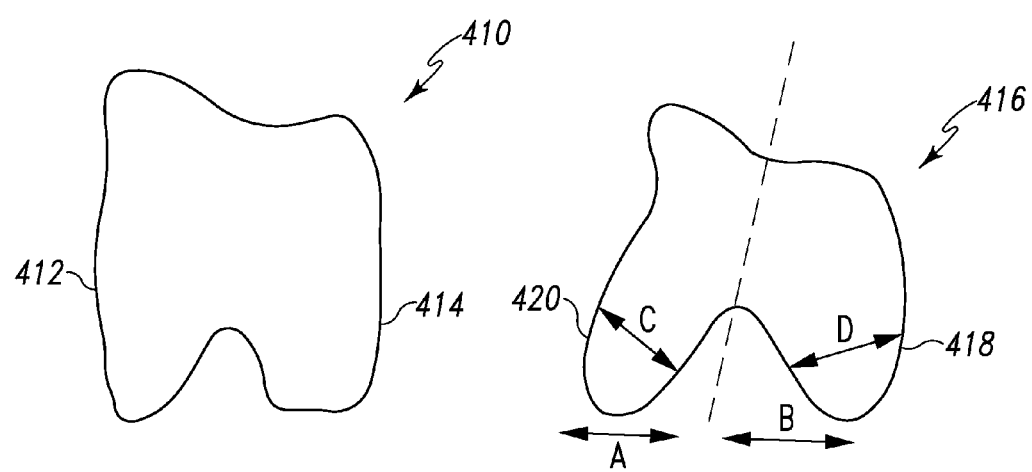
FIG. 53 depicts a femoral component with non-divergent condyle areas that may be used in a system of the present invention.
FIG. 54 depicts a femoral component with divergent condyle areas that may be used in a system of the present invention.

The present invention includes configurations for a variety of condyle geometries. FIG. 53 depicts a femoral component 410 with condyle areas 412 and 414. Condyle areas 412 and 414 in this embodiment are non-divergent. FIG. 54 shows femoral component 416 with medial condyle area 418 and lateral condyle area 420. Condyle areas 418 and 420 in this embodiment are divergent. In addition, the condyle areas may be designed to diverge equally (distance "A" of FIG. 54=distance "B" of FIG. 54), or one condyle area may diverge more than the other condyle area (distance "A" of FIG. 54>distance "B" of FIG. 54). In the embodiment of FIG. 54, the medial condyle area 418 is also wider than lateral condyle area 420 (distance "C" of FIG. 54<distance "D" of FIG. 54). Alternatively, condyle areas could be made to be equal (distance "D" of FIG. 54=distance "C" of FIG. 54).

Figure 55:
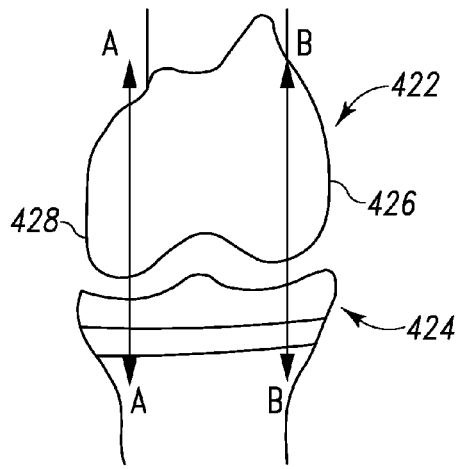
FIG. 55 depicts a tibial component and a femoral component with asymmetrical condyle areas that may be used in a system of the present invention.

FIG. 55 depicts the femoral component 422 and tibial component 424 of a knee replacement wherein the femoral component 422 has an asymmetry. More specifically, lateral condyle area 426 has a larger radius than medial condyle area 428. This is shown more clearly in FIG. 56 and FIG. 57.

Figure 56:
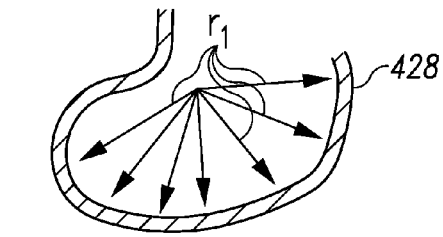
FIGS. 56 and 57 depict cross-sections of the asymmetrical condyle areas in the anterior to posterior direction of the femoral component of FIG. 55.
Figure 57:
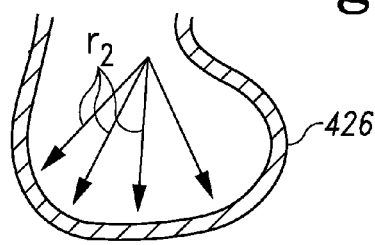

FIG. 56 is a cross-sectional view of medial condyle area 428 of femoral component 422, taken along line A-A. FIG. 56 depicts a number of radii of curvature $r_1$ from a central point to the inner surface of medial condyle area 428. FIG. 57 is a cross-sectional view of lateral condyle area 426 of femoral component 422, taken along line B-B. FIG. 57 depicts a number of radii of curvature $r_2$ from a central point to the inner surface of lateral condyle area 426. Comparison of the medial radii $r_1$ to lateral radii $r_2$ shows that the radius of curvature of the medial condyle area 428 is smaller than the radius of curvature of the lateral condyle area 426 (in general, $r_1$ is less than $r_2$).

Figure 58:
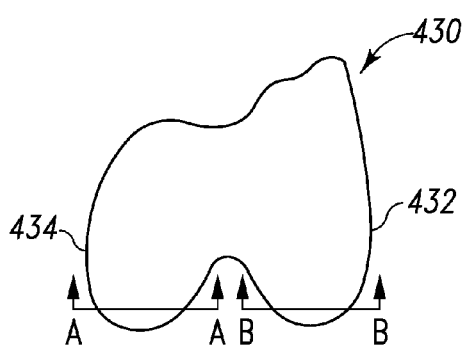
FIG. 58 depicts an alternative embodiment of a femoral component with asymmetrical condyle areas that may be used in a system of the present invention.

Similarly, the radius of curvature in the plane orthogonal to the cross-sections of FIG. 56 and FIG. 57 may vary. FIG. 58 depicts femoral component 430 which comprises lateral condyle area 432 and medial condyle area 434 wherein the femoral component 430 has an asymmetry in this orthogonal plane, that is, from side to side of the respective condyle areas. This is shown more clearly in FIG. 59 and FIG. 60.

Figure 59:
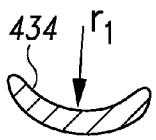
FIGS. 59 and 60 depict cross-sections of the asymmetrical condyle areas in the medial to lateral direction of the femoral component of FIG. 58.
Figure 60:
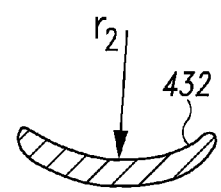

FIG. 59 is a cross-sectional view of medial condyle area 434 of femoral component 430 taken along line A-A of FIG. 58. FIG. 59 depicts the radius of curvature $r_1$ from side to side of medial condyle area 434. FIG. 60 is a cross-sectional view of lateral condyle area 432 of femoral component 430, taken along line B-B of FIG. 58. FIG. 60 depicts the radius of curvature $r_2$ from side to side of lateral condyle area 432. Comparison of the medial radius $r_1$ to lateral radius $r_2$ shows that the radius of curvature of the medial condyle area 434 is less than that of the lateral condyle area 432 ($r_1$ is less than $r_2$).

Figure 61:
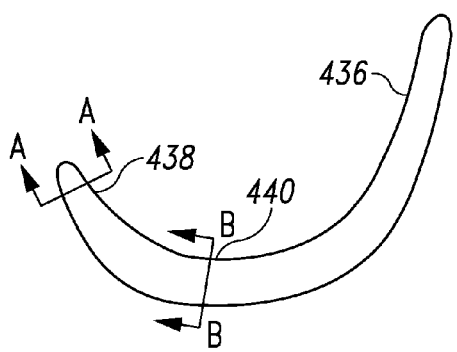
FIG. 61 depicts the sagittal view of a femoral component with different radii of curvature from the anterior to posterior portions of the component that may be used in a system of the present invention.
Figure 62:
FIGS. 62 and 63 depict cross-sections in the medial to lateral direction of the femoral component shown in FIG. 34.
Figure 63:
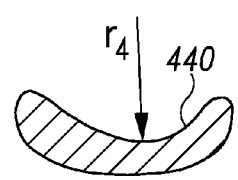

It should be further noted that the radius of curvature at different cross-sections of each condyle area from the anterior to the posterior of the condyle area may vary. FIG. 61 shows a femoral component 436 that varies in such a manner. The cross-sections and radius of curvature for line A-A of FIG. 58 at a posterior portion 438 of the femoral component 436 and line B-B of FIG. 58 at a more anterior portion 440 of the femoral component 436 are shown in FIGS. 62 and 63, respectively. Comparison of the radii shows that the radius $r_3$ of the posterior portion 438 is smaller than the radius $r_4$ of the anterior portion 440.

An alternative to providing components with geometries specifically adapted to a particular condyle in accordance with the present invention is to adapt the position and orientation of a single component to the particular geometry of the condyle. This is explained with reference to FIGS. 64, 65 and 66. FIG. 64 shows a femur 442 with a PFJ component 444 and a condylar component 446 implanted on the lateral condyle of the femur 442. The PFJ component 444 includes a medial node 445. The track of the patella across the femur 442 as the leg goes from extension to flexion is indicated by patellar track 448. The track of the tibia across the femur 442 as the leg goes from extension to flexion is indicated by tibial track 450. The condylar component 446 is positioned such that the tibial track 450 lies along the longest portion of the condylar component 446.

FIG. 65 shows a femur 452 with a PFJ component 454 and a condylar component 456, which is identical to the condylar component 446, implanted on the medial condyle of femur 452. The PFJ component 454 is identical to the PFJ component 444 except that the PFJ component 454 includes both a medial node 455 and a lateral node 457. The track of the patella across the femur 452 as the leg goes from extension to flexion is indicated by the patellar track 458. The track of the tibia across the femur 452 as the leg goes from extension to flexion is indicated by the tibial track 460. The condylar component 456 is positioned such that the tibial track 460 lies along the longest portion of the condylar component 456.

The PFJ area of the femur 452 is, for purposes of this example, identical to the PFJ area of the femur 442. Moreover, the patella track 448 and the patella track 458 are identically oriented on the respective femurs. Thus, because the PFJ components 444 and 454 are identical components, with the exception of the absence of a lateral node on the PFJ component 444, they have been implanted in identical positions on the femurs 442 and 452. However, the medial condyle of the femur 442 is lower than the medial condyle of the femur 452. Additionally, the tibial track 456 is skewed when compared with the tibial track 446. This is shown more clearly in FIG. 66.

FIG. 66 is an overlay of the components of FIGS. 64 and 65 on the femur 452. FIG. 66 thus shows the femur 452, the PFJ component 454, the condylar component 456 and the patella track 460 of FIG. 65. Under the conditions set forth above, juxtaposition of the components of FIG. 64 on FIG. 66, results in the PFJ component 444 aligning exactly with the PFJ component 454 with the exception of the lack of a lateral node on the PFJ component 444. This is indicated in FIG. 66 by the dashed reference line 444.

FIG. 66 further shows the position of condylar component 446 and the tibial track 450 with the same alignment with the PFJ component 444 as shown in FIG. 64. However, even though the condylar component 456 is identical to the condylar component 446, FIG. 66 shows that the condylar component 456 is positioned closer to the PFJ component 454 than the condylar component 446 is positioned to the PFJ component 456. Additionally, the condylar component 456 is rotated in a slightly counter-clockwise direction compared to the condylar component 446.

Thus, in accordance with the present invention, the position and orientation of a component on a femur may be adapted to optimize the performance of the component on the femur. Moreover, while the above discussion of condyle geometries used examples of condyle areas within certain unibody components, the geometries may be practiced with condyle components as well as components having condylar areas.

Unibody Femoral Component

While it is generally beneficial to use smaller components during replacement surgery, there may be instances where a full unibody femoral component is desired to be implanted. FIG. 67 shows a femoral component 462 which comprises a PFJ area 464, a medial area 466 and a lateral area 468.

Figure 68:
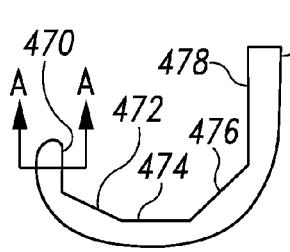
FIGS. 68, 69 and 70 depict various possible configurations of the interior of the component of FIG. 67 in the anterior to posterior direction.
Figure 69:
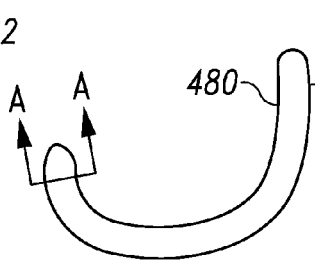
Figure 70:
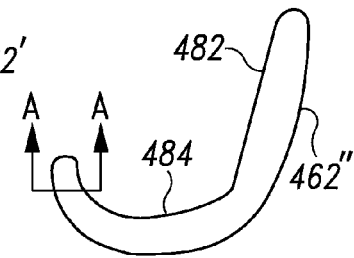

In accordance with the present invention, the femoral component 462 may include a variety of internal geometries. FIG. 68 shows the femoral component 462 with a faceted interior in the anterior to posterior direction comprising flat surfaces 470, 472, 474, 476 and 478. FIG. 69 shows the femoral component 462' with a curved interior surface 480. FIG. 70 shows the femoral component 462" with a combined curved and flat interior comprising flat surface 482 and curved surface 484.

Figure 71A:
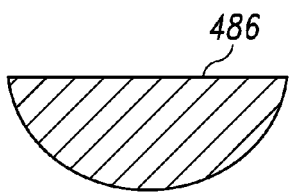
FIGS. 71A, 71B, 71C, 71D and 71E depict various cross-sections in the medial to lateral direction that may be used in the component of FIG. 67.
Figure 71B:
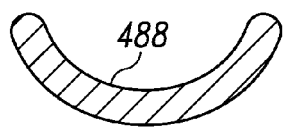
Figure 71C:
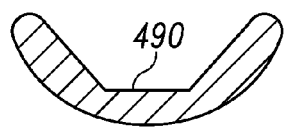
Figure 71D:
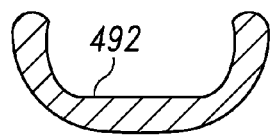
Figure 71E:

Moreover, the interior surfaces of the femoral component 462 may be constructed with a variety of geometries in the medial to lateral direction. By way of example, but not of limitation, FIG. 71A shows a flat cross-section 486 taken across line A-A of FIGS. 68, 69 or 70. FIG. 71B shows a curved interior 488 while FIG. 71C shows a faceted interior 490. FIG. 71D shows an interior 492 with curved sides and a flat bottom while FIG. 71E shows an interior 494 with flat sides and a curved bottom. These shapes accommodate local bone geometry better than previous known shapes and enable the surgeon to leave more healthy bone in the joint.

Figure 72:
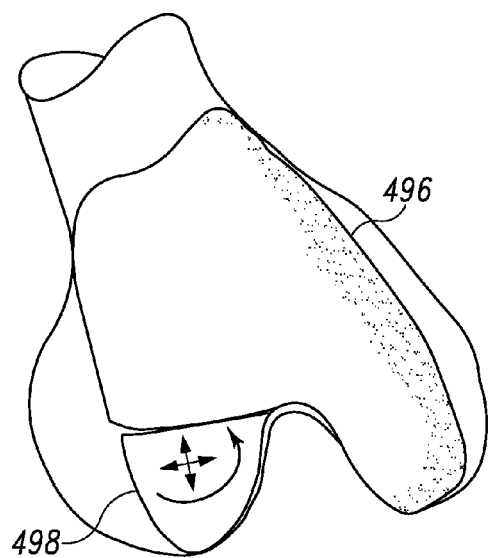
FIG. 72 illustrates the six degrees of freedom in placement of replacement components made possible by a system of the present invention.

As understood from the above descriptions and accompanying drawings, the system of the present invention provides a total or bi-compartmental knee comprised of components that may be implanted with six degrees of freedom. Specifically, with reference to the PFJ/medial condyle component 496 as shown in FIG. 72, a condylar component 498 may be moved upwardly, downwardly, to the left, to the right, or rotated to the left or to the right. Consequently, different patient geometries may be addressed without requiring a different component geometry for every possible patient geometry or requiring that the surgeon conform the bone to a component geometry by removing healthy bone. Instead, the surgeon may select a slightly different place of implantation or component orientation to accommodate patient bone geometry.

Exemplary Methods

One advantage of the system described herein is that it allows the surgeon to build a custom implant for each patient. Currently, implant systems are offered in a limited number of discrete sizes that most likely will not be precisely the size needed for a patient. For example, a patient's knee may measure 75-mm. However, available implants for this patient may measure 70-mm and 80-mm.

The surgeon in these instances typically uses a single cutting block that is designed for the replacement component. The cutting block is placed either against the posterior of the femur or against the anterior of the femur and provides guides for making four resections of the femur, two resections on the posterior side and two resections on the anterior side. Accordingly, the surgeon must choose to optimize the cuts either for the anterior fit or posterior fit of the component, or to split the misfit.

In any event, the surgeon has to choose between an implant that is too small or too big. This can adversely affect that outcome of the procedure. The implant system described in this invention would allow the surgeon to build an implant that is exactly 75-mm. Also, the surgeon can do this without having the added expense of a large inventory that includes many sizes.

Figure 73:
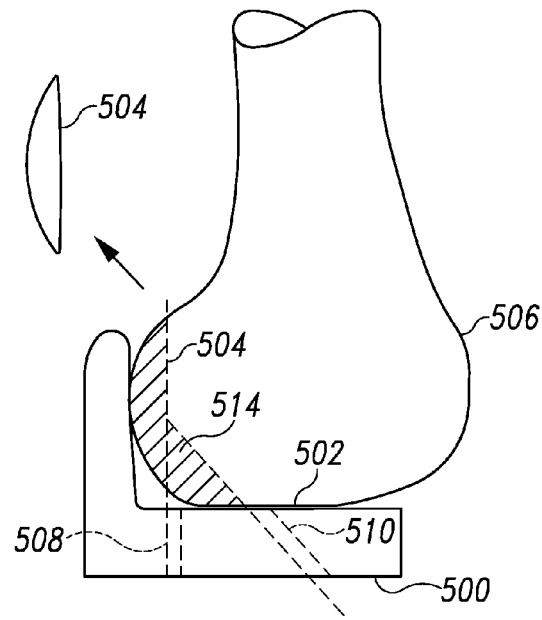
FIG. 73 depicts a cutting guide block placed in position for resecting the posterior portion of a femur in accordance with the present invention.
Figure 74:
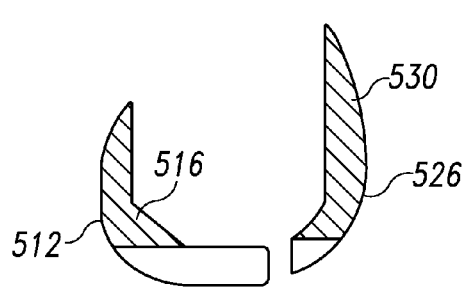
FIG. 74 depicts components that have been selected for use in an implant in accordance with the present invention.

In order to perform a custom implant in accordance with principles of the present invention, a surgeon first decides which areas of bone will be replaced. For purposes of this example, the anterior, posterior and distal portions of the femur will be resected. Accordingly, the surgeon makes a first cut in the distal end of a femur. Next, as shown in FIG. 73, a surgeon locates a first cutting block 500 adjacent to the resected distal end 502 and the posterior portion 504 of the femur 506. The cutting block 500 comprises cutting guides 508 and 510, which ensure that the resected posterior sections of the femur 506 will match the dimensions of a component 512 shown in FIG. 74. More specifically, the shaded portion 514 of the femur 506 will match shaded portion 516 of the component 512. The shaded portion 514 of the femur 506 is then resected. Thus, the locations of the cuts at the posterior area of the femur 506 are determined as a function of the posterior boundary of the femur 506. Accordingly, when the component 512 is attached to the femur 506, the outer boundary of the component 512 will mimic the natural outer boundary of the posterior of the femur 506.

Figure 75:
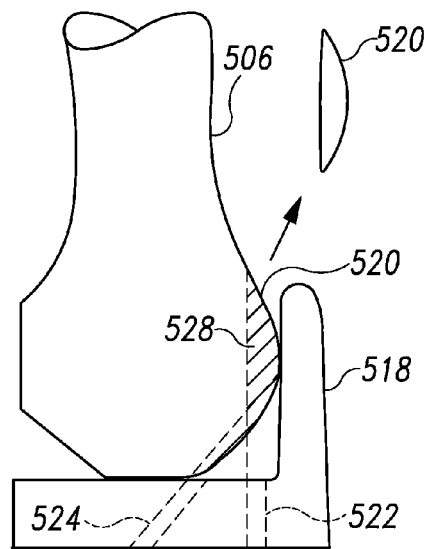
FIG. 75 depicts a cutting guide block placed in position for resecting the anterior portion of the femur of FIG. 73 in accordance with the present invention.

The surgeon then places a second cutting block 518 in position to resect the anterior portion 520 of the femur 506 as shown in FIG. 75. The cutting block 518 includes the cutting guides 522 and 524, which ensure the resected anterior areas of the femur 506 will match the dimensions of the component 526 shown in FIG. 74. More specifically, the shaded portion 528 of the femur 506 will match the shaded portion 530 of the component 526. The anterior sections of the femur 506 are then cut, leaving the femur 506 in the configuration depicted in FIG. 76. Thus, the locations of the cuts of the anterior area of the femur 506 are determined as a function of the anterior boundary of the femur 506. Accordingly, when the component 526 is attached to the femur 506, the outer boundary of the component 526 will mimic the natural outer boundary of the anterior of the femur 506.

Next, the width of the femur from point A to point B (see FIG. 76) is measured and retained for future use. This measurement is called the anterior-posterior (AP) measurement. The bone is then prepared to receive the component 512 and the component 526 by boring hole 532 and another hole (not shown). Next, the component 512 and the component 526 are placed in position abutting the femur 506 as shown in FIG. 77, and screws 534, 536, and two other similar screws (not shown) are inserted and torqued. The screws 534 and 536 and the two other screws are torqued until the AP measurement, the distance from point A to point B in FIG. 77, measures about 0.001 to 0.5 inches less than the initial AP measurement. This ensures that a good press fit of the implants will be realized while closely mimicking the size of the femur 506 prior to resection.

Once the components have been properly torqued, thereby clamping the femur 506 between the component 512 and the component 526, a gap 538 between the components 512 and 526 may remain. The gap 538 represents the difference in the diameter of the femur 506 and the combined diameter of the components 512 and 526. Accordingly, the present method allows for the outer boundary of replacement components to mimic the outer diameter of the natural bone even for irregular diameters. In accordance with the present invention, the components 512 and 526 may be configured such that the gap 538 is not located on a load line. If desired, the surgeon may fill this gap with an acceptable material such as materials herein described with respect to bone tides.

Accordingly, by providing a plurality of cutting blocks, each block optimized for particular components, and by using components such as components 512 and 526, a custom fit may be realized for a patient, regardless of the patient's knee size. Thus, in accordance with the systems and methods of the present invention the size of the implanted components may be customized. Moreover, the plurality of cutting blocks may each provide for bone preparation to fit components having different internal geometries. Thus, the surgeon has additional freedom in optimizing each resection for a particular patient. Moreover, by using components such as components 512 and 526, the femoral components may be clamped to the bone, thereby providing improved fixation of the components to the bone.

In accordance with an alternative method, a femur is prepared to receive an implant by making a series of parallel cuts in the femur. Typically, a bone is prepared by locating a box on the bone, and a guide is selected and positioned with in the box. The guide is configured to fit within the box at a certain distance from the side of the box. A number of guides are available for use in the box, each guide configured to fit within the box at a distance from the side of the box different from the other guides. Thus, a guide is selected based upon the amount of the bone that is to be resected. After the resection is made, the box is moved to provide another cut.

However, in accordance with one embodiment of the present method, a second parallel cut is made using a second guide prior to moving the box. This is beneficial in that once the box is positioned, making additional cuts parallel to the first cut is easily accomplished by simply using additional guides.

This method is enabled by the provision of replacement components with multiple parallel inner surfaces. Two such components are shown in FIG. 78. The PFJ 540 and the unicondylar component 542 are shown as they would be positioned when implanted on a femur (not shown). The PFJ component 540 includes the inner surfaces 544, 546 and 548. The unicondylar component 542 includes the inner surfaces 550, 552, 554 and 556. In this embodiment, the inner surfaces 544, 546 and 548 of PFJ 540 are parallel to inner surfaces 550, 556 and 554, respectively, of unicondylar component 542. Thus, for example, when the box is positioned to make a cut in the femur that will fit with inner surface 544, by using a second guide, the cut in the femur that will fit with inner surface 550 may also be made without moving the box.

Figure 79A:
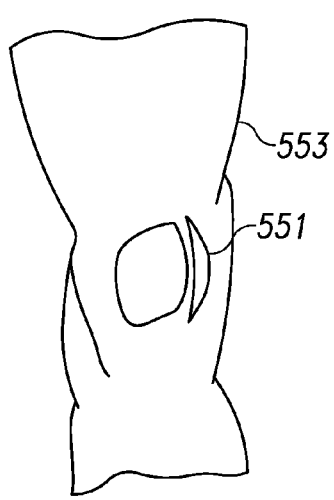
FIGS. 79A-D depict an implantation procedure for a patellofemoral component in accordance with the present invention.
Figure 79B:
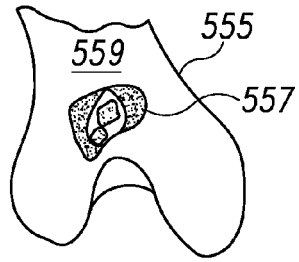
Figure 79D:
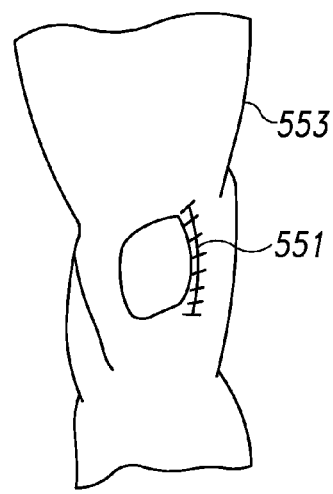
Figure 79C:
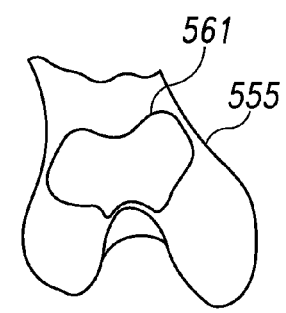

In accordance with a further method, a femoral prosthesis system is incrementally implanted into a femur of a patient over a number of spaced apart surgical procedures. With reference to FIG. 79A, during a first surgical procedure, an incision 551 is made in the leg 553 of a patient. As shown in FIG. 79B, the femur 555 of the patient includes a diseased portion 557 that is located generally in the patellofemoral joint area 559 of the femur 555. Accordingly, during the first surgical procedure, the diseased portion 557 is resected, along with a minimal amount of healthy bone. Next, a replacement patellofemoral joint component 561 is advanced through the incision 551 and implanted into the resected area of the patellofemoral joint as shown in FIG. 79C. The incision 551 is then closed as shown in FIG. 79D.

Figure 79E:
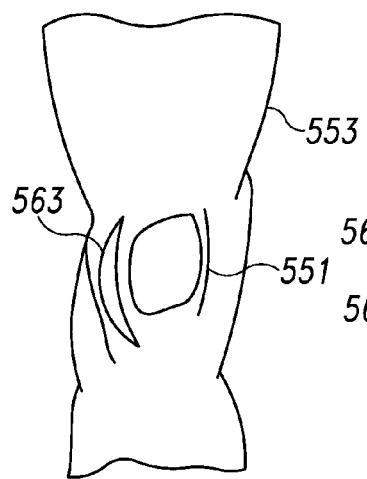
FIGS. 79E-H depict an implantation procedure for a condylar component adjacent to the patellofemoral component implanted during the procedure of FIGS. 79A-D.
Figure 79F:
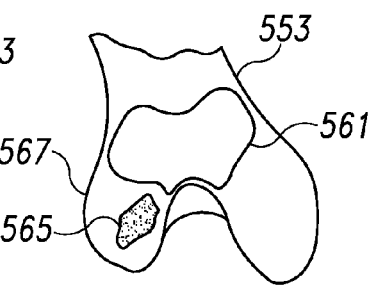
Figure 79H:
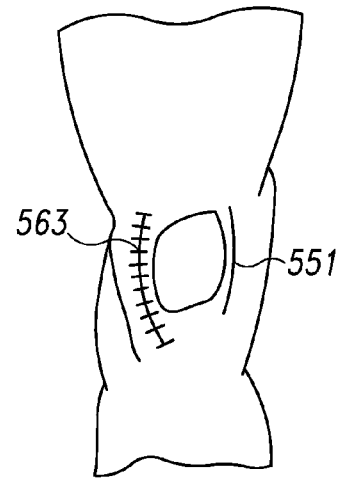
Figure 79G:
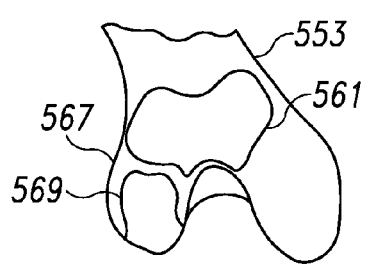

During a second surgical procedure, an incision 563 is made in the same leg 553 of the same patient as shown in FIG. 79E. The incision 563 is made in this example on the opposite side of the leg 553 as the incision 551 so as to allow access to the diseased portion 565 of the medial condyle 567 shown in FIG. 79F. After the diseased portion 565 is resected, along with a minimal amount of healthy bone in the medial condyle 567, a replacement medial condyle component 569 is implanted in the medial condyle 567 as shown in FIG. 79G.

In accordance with principles of the present invention, the medial condyle component 569 is implanted in the medial condyle 567 adjacent to, but spaced apart from, the patellofemoral component 561. Alternatively, the medial condyle component 569 may be implanted in the medial condyle 567 adjacent to and abutting the patellofemoral component 561. In either event, spacers, which may be integral to the components, may be used to reduce the production of wear debris and removal or replacement of the patellofemoral component 561 is not required.

Those of ordinary skill in the art will appreciate that the foregoing procedures may be reversed such that the condylar component is implanted in the first procedure and the patellofemoral joint component is implanted in the second procedure. Moreover, additional components may be implanted either in conjunction with the foregoing procedures or during procedures either before or after the foregoing procedures. Thus, in accordance with principles of the present invention, a surgeon need only replace the diseased portion of a femur. Furthermore, in the event another portion of the femur becomes diseased at a later time, the newly diseased portion may be replaced without removing the previously implanted component.

In a further embodiment, the prosthesis system is assembled ex vivo and then implanted as a unit. In accordance with this method, an incision 900 is made in a leg 902 as shown in FIG. 80A. The incision 900 exposes the femur 904 shown in FIG. 80B. After making any desired measurements, the portion of the femur 904 to be resected is determined and the placement of the cuts is determined as indicated by the dashed line 906. The femur 904 is then resected resulting in the configuration shown in FIG. 80C.

In conjunction with the determination of the portion of the femur 904 to be resected, a PFJ component 908 (see FIG. 80D) is selected, preferably from a kit comprising a variety of PFJ components of varying dimensions. The PFJ component 908 includes an outer articulating surface 910, an inner bone mounting surface 912 and a side 914 that includes a connector receptacle (not shown). The PFJ component 908 is selected to closely approximate the geometry of the PFJ portion of the femur 904 in a healthy state.

A condylar component 916 having an outer articulating surface 918, an inner bone mounting surface 920 and a side 922 that includes a connector receptacle (not shown) and a resilient connector 924 are further selected. In this example, the resilient connector 924 includes an integrally formed spacer 926.

The PFJ component 908 and the condylar component 916 are then connected using the resilient connector 924 such as by insertion of the resilient connector 924 into the connector receptacles (not shown) in the side 914 of the PFJ component 908 and the side 922 of the condylar component 916. The connection of the PFJ component 908 and the condylar component 910 results in the prosthesis system 928 shown in FIG. 80E. In the prosthesis system 928, the PFJ component 908 is resiliently connected to, but spaced apart from, the condylar component 916 by the resilient connector 924.

The prosthesis system 928 is then inserted through the incision 900 and mounted onto the femur 904. Accordingly, as shown in FIG. 80F, the bone mounting surface 912 of the PFJ component 908 and the bone mounting surface 920 of the condylar component 916 are mounted on the femur 904. Additionally, the side 914 of the PFJ component 908 is in opposition to the side 922 of the condylar component 916. Because of the spacer 926 on the resilient connector 924, however, a gap, generally indicated by the arrow 930, exists between the adjacent PFJ component 908 and condylar component 916. The gap may be filled with any acceptable filler material such as bone was or bone cement. The method ends with the closing of the incision 900 as shown in FIG. 80G.

Guides and Instruments

Traditionally, bone preparation for a total or partial knee prosthesis has relied upon the use of the above discussed box and guides along with an oscillating saw and blade. Thus, a surgeon presented with a defective area 558 shown in FIG. 81, would traditionally make a cut on the femur 560 as indicated by the dashed line 562, resecting the entire anterior portion of the condyle 564. For traditional replacement components, this approach to resection is very effective. However, such an approach results in a large resection of healthy sections of bone.

In order to provide more flexibility than available with traditional tools, there has recently developed a trend to use other types of instruments in removing bone. Such tools include hi-speed burrs, rasps, osteotomes and routers. The increased flexibility provided by these newly used tools includes the ability to limit surgical resection to only those areas of the bone that actually need to be replaced. Thus, with reference to FIG. 81, resection of femur 560 may be limited to defective area 558 and a minor amount of healthy bone. This ability is complimentary to the various components described above, as the resection of bone can be limited to an area that corresponds to a selected component.

Figure 82A:
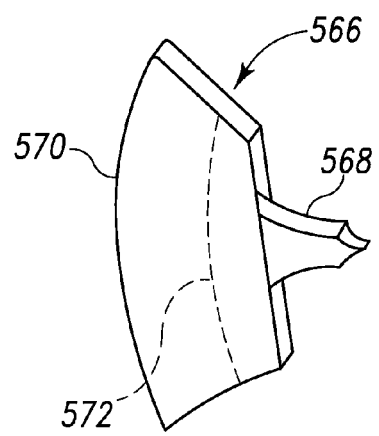
FIG. 82A depicts a cutting guide that may be used in accordance with the present invention to resect the defective area of FIG. 81.
Figure 82B:
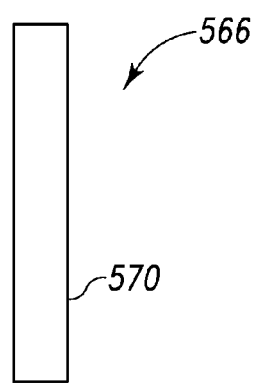
FIG. 82B depicts a top perspective view of the guide of FIG. 82A.
Figure 82C:
FIG. 82C depicts a top perspective view of a component that may be implanted into the femur of FIG. 81 after using the guide of FIG. 82A to resect the defective area of FIG. 81 in accordance with the present invention.

The present invention includes a number of guides that may be used to assist in performing such resection. One such guide is shown in FIG. 82A. The guide 566 includes a pin 568, a guide surface 570 and a tide mark 572. The pin 568 is used to anchor the guide 566 in a bone. Positioning of the guide 566 within a bone may be done using computer aided surgery. The tide mark 572 is used to indicate the depth to which the guide 566 is to be inserted into the bone. The tide mark 572, which may be erasable, may be determined using computer aided modeling. Referring now to FIG. 82B, the guide surface 570 is generally sized and contoured to match the curvature and general shape of a replacement component such as the component 574 shown in FIG. 82C.

Figure 81:
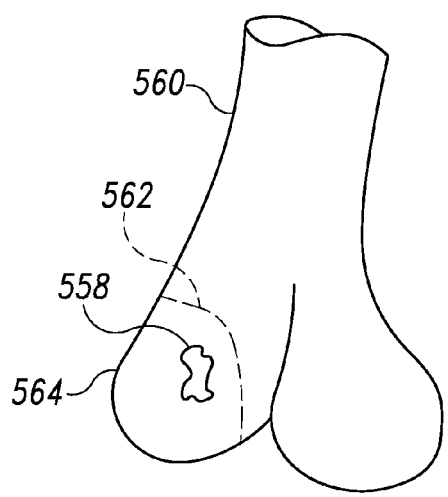
FIG. 81 depicts a femur with a defective area.

Exemplary use of the guide 566 is explained with reference to FIG. 81. Initially, the defective area 558 and the femur 560 are modeled. Based upon this modeling, it is determined that the replacement component 574 is slightly larger than the defective area 558 and matches the general contour of the femur 560 in the vicinity of the defective area 558. Thus, the guide 566, which correlates with the component 574, is identified as the appropriate guide to be used. Accordingly, the location of the tide mark 572 on the guide 566 is determined as a function of the thickness of the component 574. The system will further identify, in this embodiment, a burr head size to be used with the guide 566.

Figure 83:
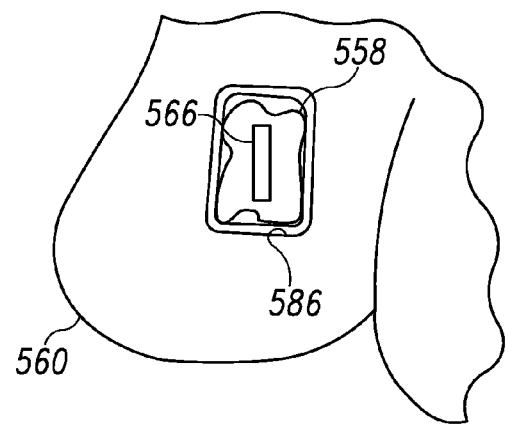
FIG. 83 depicts the guide of FIG. 82A inserted into the femur of FIG. 81.
Figure 84:
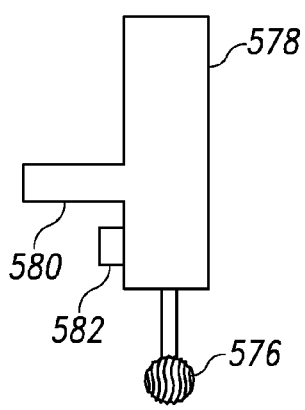
FIG. 84 depicts a tool that may be used with the guide of FIG. 82A to resect a portion of the femur of FIG. 81 in accordance with the present invention.
Figure 85:
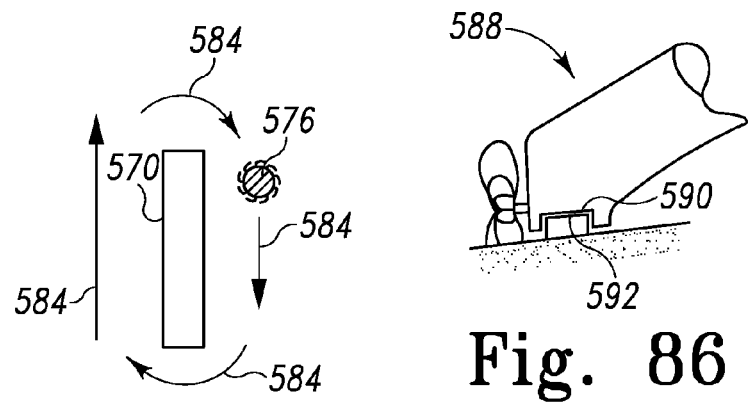
FIG. 85 depicts a path using the guide of FIG. 82A along which the tool of FIG. 84 may be moved to define the area of the femur of FIG. 81 to be resected in accordance with the present invention.

After marking the guide 566 with the tide mark 572, the guide 566 is inserted into the femur 560 as shown in FIG. 83. Placement of the guide 566 into the femur 560 may be computer aided. The burr head identified for use, such as burr head 576 shown in FIG. 84, is inserted into a hi-speed burr tool 578. The hi-speed burr tool 578 includes a guide surface rest 580 and a roller 582. The hi-speed burr tool 578 is then energized and the guide surface rest 580 is placed on the guide surface 570 with the roller 582 on the side of the guide 566. The surgeon then guides the hi-speed burr tool 578 around the periphery of the guide 566, as indicated by the arrows 584 in FIG. 85, creating a channel 586 in the femur 560 around the defective area 558 as shown in FIG. 83. The channel 586 may be made in one continuous cut or in a series of cuts. The surgeon then removes the guide 566, and excises the bone within the area defined by the channel 586 to the depth of the channel 586.

As stated above, the guide 566 is generally in the shape of the replacement component 574. Thus, selection of a burr head of an appropriate size results in the outer wall of the channel 586 conforming to the size and shape of the replacement component 574 while completely excising the outer boundaries of the defective area 558. Moreover, the depth of the resection is determined by the insertion of the guide 566 to the depth of the tide mark 572 and the height of guide surface rest 580 above the bottom of burr head 576. Thus, the depth of the resection may be established to coincide with the thickness of the replacement component 574.

Figure 86:
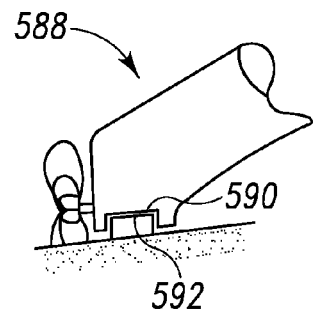
FIG. 86 depicts an alternative tool and guide that may be used to define the area of the femur of FIG. 81 to be resected in accordance with the present invention.

By providing burr heads of different sizes, a single guide may be used with different replacement components of different widths and heights. Alternatively, the standoff distance between the edge of the roller 582 of the hi-speed burr tool 578 and the outer periphery of the burr head 576 may be variable to accomplish the same functionality. Similarly, the height of the guide surface rest 580 may be adjustable to provide resection of different depths. The instrument may also be configured as a side cutting instrument such as the side cutting tool 588 shown in FIG. 86. The side cutting tool 588 includes a channel 590 which is configured to accept the guide surface 592. In some embodiments, the guide surface 592 is in the form of a continuous ridge about the periphery of a guide.

Those of ordinary skill in the relevant art will appreciate that the outer perimeter of the guide surface may be formed in a variety of shapes to accommodate replacement components of various shapes. Additionally, the outer perimeter may include curvature in multiple axes to provide, for example, for use on the ball shaped area of a bone. These and other permeations are within the scope of the present invention.

Figure 87:
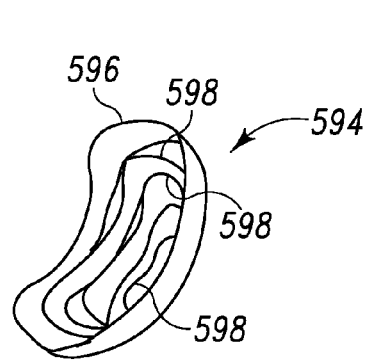
FIG. 87 depicts a punch guide that may be used to define the area of a bone to be resected in accordance with the present invention.
Figure 88:
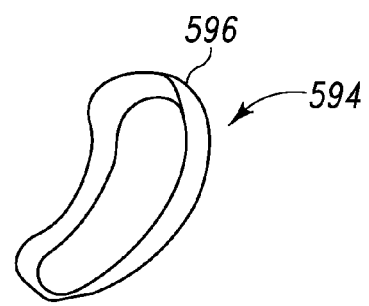
FIG. 88 depicts the punch guide of FIG. 87 with the internal cutting edges removed for clarity.

An alternative embodiment of a guide is shown in FIG. 87. The guide 594 is a punch guide. The guide 594 includes an outer cutting edge 596, and a plurality of internal cutting edges 598. For clarity of explanation, FIG. 88 shows the guide 594 with the internal cutting edges 598 removed. The outer cutting edge 596 is shaped to conform to the outer shape of a replacement component. The height of the outer cutting edge 596 conforms to the thickness of the replacement component. Each of the internal cutting edges 598 may be separately shaped and sized to conform to internal contours and thicknesses of the replacement component. Thus, when forced against a bone, the outer cutting edge 596 and each of the internal cutting edges 598 cut into the bone. The guide 594 may then be removed, leaving a series of cuts in the bone that conform to the shape, contour and thickness of the replacement component. By using a tool to excise the bone down to the level of the cuts, a bone can be resected to receive the replacement component. In an alternative embodiment, a guide only includes the outer cutting edge 596.

Figure 89:
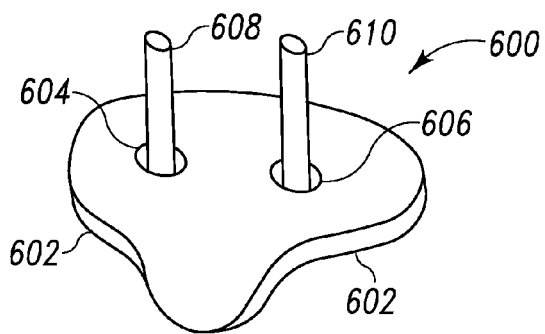
FIG. 89 depicts an alternative punch guide positioned on guide pins that may be used to define the area of a bone to be resected in accordance with the present invention.

Placement of a punch guide may be facilitated according to a variety of alternative methods. One method uses the device shown in FIG. 89. The guide 600 includes a cutting edge 602 around the periphery of the guide 600 and guide holes 604 and 606. The guide 600 may further include internal cutting edges. The guide 600 is shown inserted onto pins 608 and 610 which extend through the holes 604 and 606, respectively. In practice, the pins 608 and 610 are inserted into a bone. The guide 600 is then positioned over the pins 608 and 610 aligning the holes 604 and 606 with the pins 608 and 610. The guide 600 is then moved against the bone. Thus, the guide 600 is located in the desired position. The method using the guide 600 may then proceed in a manner similar to that described in reference to the guide 594.

The depth of the cut made by the guide 600 may be established in a number of ways. For example, the depth of the cut may be established by the depth of the cutting edge 602, by marking the desired depth on the cutting edge 602, by a tide mark on the pins 608 and 610, or by providing stops on the pins 608 and 610 beyond which the guide 600 cannot be moved. Placement of the pins 608 and 610 may be accomplished using computer aided surgery or other imagery assisted techniques to ensure proper depth and location of the cut.

Alternatively, a previously implanted component whose position on a femur is known may be used along with a pin guide to place the pins that are used to align a guide. Such a pin guide is discussed in reference to FIG. 90, wherein a unitrial component 612 is implanted in the femur 614. The unitrial component 612 includes the holes 616 and 618.

Figure 90:
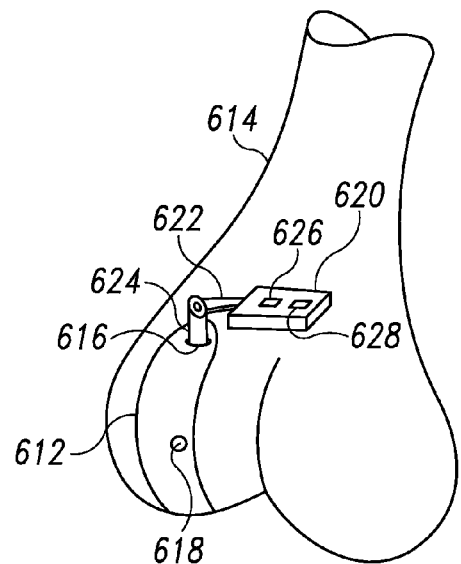
FIG. 90 depicts a pin guide mounted on an implanted component that may be used to position pin guides in accordance with the present invention.

A pin guide 620 is also shown in FIG. 90. In this embodiment, the pin guide 620 includes a swing arm 622, a base arm 624 and pin guide holes 626 and 628. The base arm 624 is configured to be inserted into the hole 616 of the unitrial component 612. Moreover, the base arm 624 and the hole 616 are configured to provide a known orientation of the base arm 624 with respect to the orientation of the unitrial component 612. Such a configuration may include a key-lock configuration or simply a mark on the base arm 624 that is aligned with a mark on the unitrial component 612. The base arm 624 may further be adjustable in height so as to account for curvature of the bone.

A mechanism is also provided for establishing a desired orientation of the swing arm 622 with respect to the base arm 624. This may be a reference mark on one arm and a sequence of numbers on the other arm. Accordingly, a precise orientation of the pin guide 620 with respect to the femur 614 is achieved.

Specifically, modeling of the femur 614 provides the geometry of the femur 614. Imagery and subsequent modeling of the unitrial 612 provides the exact location of the hole 616 with respect to the femur 614. Because the height and orientation of the base arm 624 is known, and because the length and orientation of the swing arm 6622 is known, the precise location of the pin guide 620 with respect to the femur 614 is known. Therefore, pins may be precisely inserted into the femur 614 through the pin guide holes 626 and 628.

Alternatively, a temporary component may be placed on the femur 614 prior to any resection of the femur 614. In this alternative method of the present invention, the temporary component is imaged once it is placed. Thus, the guide pin placement, for either or both of the PFJ or condylar components, may be guided by a temporary component in a manner similar to the above described placement of the PFJ guide pins. Those of ordinary skill in the relevant art will appreciate that any number of component guide pins may be placed using this method.

Figure 91:
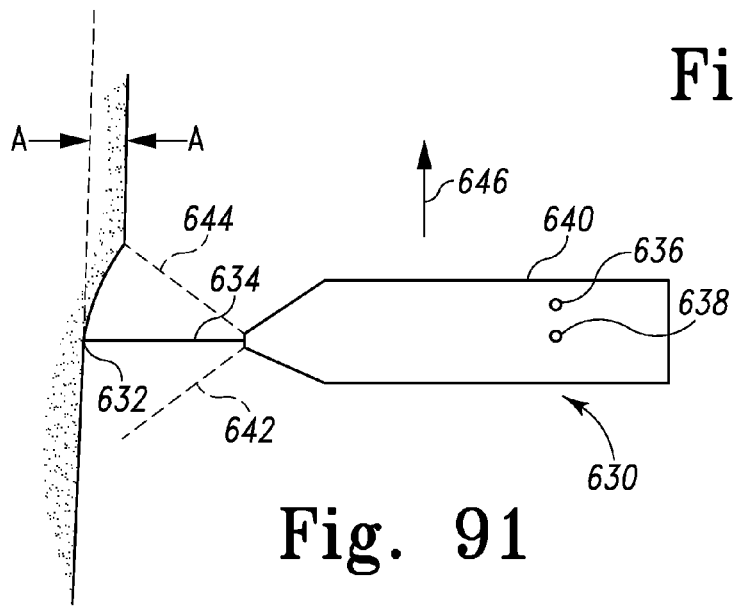
FIG. 91 depicts a saw with guide studs that may be used to resect bone in accordance with the present invention.

Certain instruments are very useful for making cuts into the planar surface of a bone. By way of example, the saw 630 shown in FIG. 91 includes an abrasive tip 632 connected to a shaft 634. Two guide studs 636 and 638 are located on the housing 640 of the saw 630. The shaft 634 moves from side to side (up and down as viewed in FIG. 91). The axes 642 and 644 show the outer limits of the arc swept by the shaft 634 through each cycle of motion.

Accordingly, when moving the saw 630 in a direction perpendicular to the axis of the housing 640, such as in the direction of the arrow 646, bone may only be cut to the depth indicated by dimension A-A with a single pass over the bone. This is referred to herein as "pass depth". The pass depth may be adjusted by providing abrasive heads of different sizes since longer heads sweep a larger arc. Moreover, a saw may be oriented to cut along the direction of travel or orthogonal to the direction of travel. Thus, a single abrasive head may provide for resections of two different widths depending upon the configuration of the abrasive head within the saw.

Figure 92:
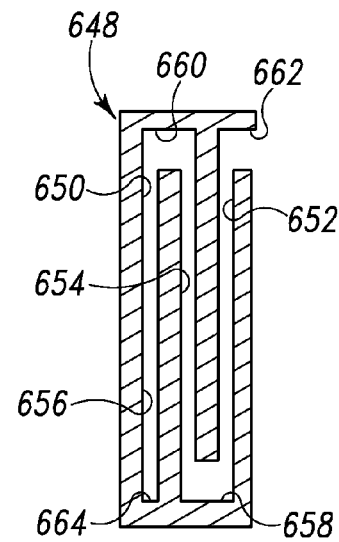
FIG. 92 depicts a guide that may be used to guide the saw of FIG. 91 to make a straight resection of a desired depth in accordance with the present invention.

The saw 630 may be used with the guide 648 shown in FIG. 92 to make cuts of a specific depth into a bone, including depths greater than a single pass depth. The guide 648 comprises a channel 650. The channel 650 is generally serpentine, consisting in this embodiment of generally parallel sub-channels 652, 654 and 656. The sub-channels 652, 654 and 656 are spaced apart at a distance up to the pass depth of the saw 630 with a particular abrasive head. The sub-channel 652 is joined to the sub-channel 654 by an end channel 658 and the sub-channel 654 is joined to the sub-channel 656 by an end channel 660. Accordingly, the channel 650 is continuous from the channel entry 662 to the channel stop 664.

Operation of the saw 630 with the guide 648 begins by identifying the area of a bone to be resected. An abrasive tip for the saw 630 is then selected. Once the abrasive head is selected, the pass depth is known, and the appropriate guide 648 may be selected.

It is contemplated within the scope of the present invention to provide a kit of sub-channels and curves that may be used to construct specific guides for use with specific resections. When performing this method with the aid of a computer program, the program may be designed to generate the design of the guide. In any event, once pass depth is known, guide sub-channel separation may be determined. Guide channel separation is selected such that the distance between adjacent sub-channels of the guide is not greater than the pass depth of the abrasive head. In one embodiment, the sub-channel separation is a function of the thickness of the wall of the guide separating adjacent sub-channels.

The kit may thus provide a plurality of sub-channel components that may be attached one to another. The sub-channel components may include a plurality of geometries to be used for various areas of a bone. Thus, curved sub-channel sections may be used for resection about the head of a femur, while relatively straight sub-channels may be used for resections limited to one area of a condyle. A computer program may be used to identify the sub-channels and curves to be used and the configuration of the components of the guide based upon modeling of the bone and the area to be resected.

Once the guide 648 is assembled or selected, it is attached to the bone to be resected with the channel entry 662 oriented away from the bone to be resected. The guide 648 is located at a height above the bone such that when the guide studs 636 and 638 are within the sub-channel 652 and against the wall of the sub-channel 652 closest to the bone, the abrasive tip will extend into the bone by the distance of one pass depth or less. Attachment of the guide 648 to the bone may be accomplished by use of a clamp, and placement of the guide 648 may be accomplished by computer guided surgery.

The guide studs 636 and 638 are then inserted into the channel entry 662 and the saw 630 is energized. The surgeon then moves the saw 630 along the channel 650, through the sub-channel 652. When both of the guide studs 636 and 638 are within the end channel 658, the saw 630 can be lowered to the sub-channel 654 and another pass made over the area to be resected.

If the area to be resected is wider than the cut possible with the saw 630, a second guide may be used adjacent the guide 648 or the guide 648 may be re-located for a second set of passes over the bone.

Figure 93:
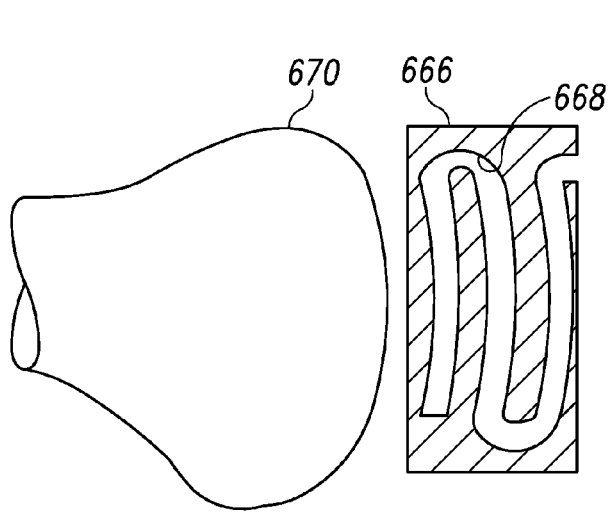
FIG. 93 depicts an alternative guide that may be used with a saw with guide studs on opposite sides of the saw housing to make curved resections of a desired depth in accordance with the present invention.
Figure 94:
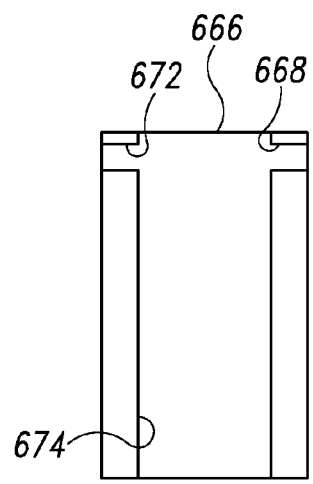
FIG. 94 depicts a top perspective view of the guide of FIG. 93.

FIG. 93 shows an alternative embodiment of a guide for use with a saw that has guide pins on opposing sides of the housing of the saw. The guide 666 includes a channel 668 that is curved, in this embodiment, to conform to the lower surface of a femur 670. The guide 666 further comprises a channel 672, shown in FIG. 94. The channels 668 and 672 are located on either side of a cavity 674. Accordingly, to use the guide 666, the opposing guide pins of a saw are inserted into the channels 668 and 672, respectively, and the abrasive tip and the saw are inserted through the opening of the cavity 674.

In one embodiment, the channels 668 and 672 are configured identically to provide a uniform cut. However, if desired, the lengths and separation of the sub-channels may be selected to provide cuts that vary in shape or depth from one side of the cut to the other side of the cut.

Figure 95:
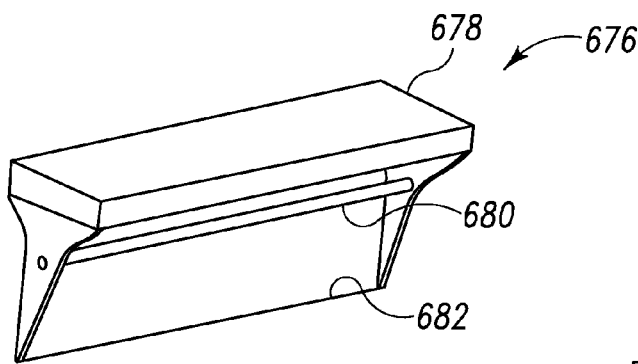
FIG. 95 depicts a wire saw that may be used to resect bone in accordance with the present invention.
Figure 96:
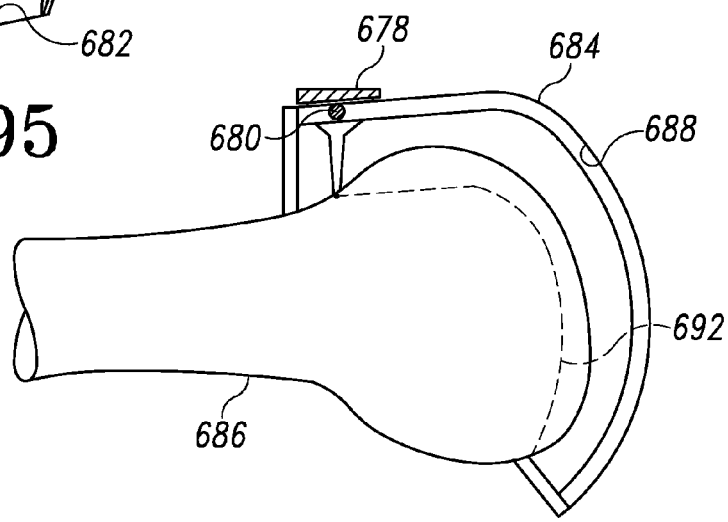
FIG. 96 depicts the saw of FIG. 95 mounted in a guide which is mounted to a femur wherein the guide enables a curved resection of the femur in accordance with the present invention.
Figures 97, 98:
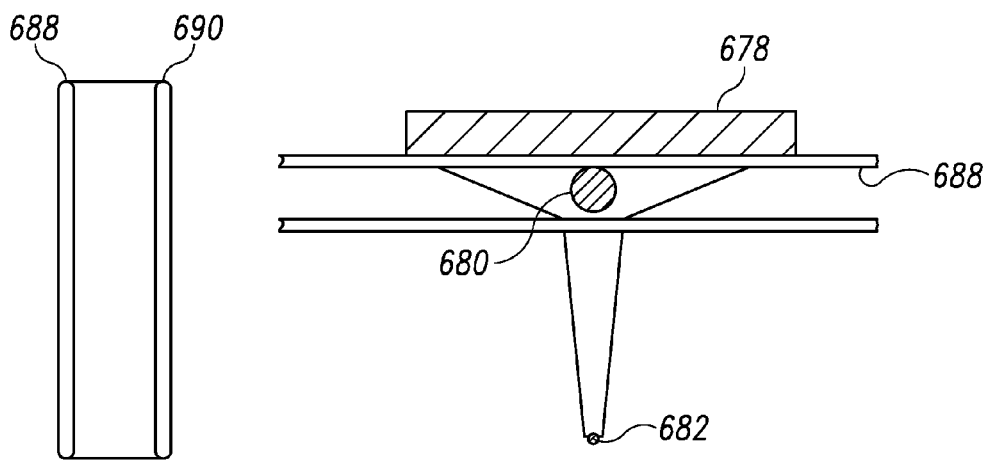
FIG. 97 depicts a top perspective view of the guide of FIG. 96.
FIG. 98 depicts an enlarged cross-sectional view of the saw of FIG. 95 mounted in the guide of FIG. 96.

A wire saw that may be used with guides incorporating features of the present invention is shown in FIG. 95. The saw 676 includes a handle (not shown), a guide platform 678, a guide pin 680 and a wire 682. The saw 676 may further include a means for moving the wire 682 such as a reciprocating means or a rotating means. The saw 676 may be used with the guide 684 shown attached to a femur 686 in FIG. 96. The guide 684 includes a channel 688 and a channel 690 shown in FIG. 97.

In operation, the guide pin 680 is inserted into the channels 688 and 690 and the guide platform 678 rests on top of the channels 688 and 690. This is shown more clearly in FIG. 98. The relatively broad base of the guide platform 678 resting on the generally parallel channels 688 and 690 ensures that the wire 682 remains perpendicular to the channels 688 and 690 during the resection. The surgeon then cuts the bone by moving the saw 676 along the channels 688 and 690. As the saw 676 is moved, the guide pin 680 constrained by the channels 688 and 690 and the guide platform 678 resting on the generally parallel channels 688 and 690 maintains the wire 682 within the femur 686 at the desired location. The use of the guide 684 results in a smoothly curved resected surface, shown as the dashed line 692 in FIG. 96.

Figure 99:
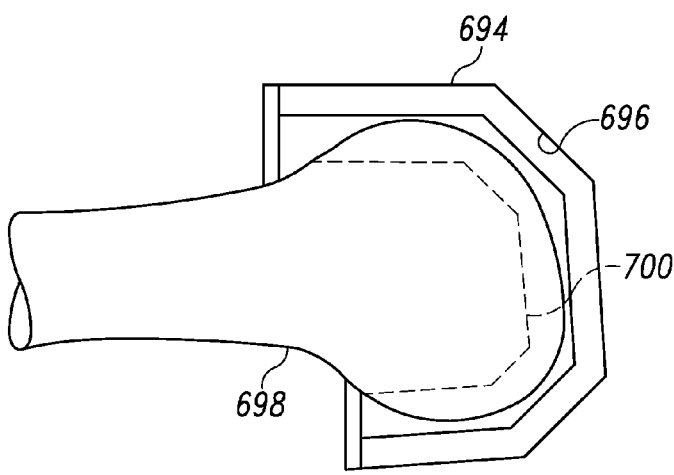
FIG. 99 depicts an alternative guide which is mounted to a femur wherein the guide enables the saw of FIG. 95 to make a faceted resection of the femur in accordance with the present invention.

Other bone surface geometries may be obtained using the principles of the present invention. By way of example, but not of limitation, the saw 676 may be used with the guide 694 shown in FIG. 99. The channel 696 of the guide 694 comprises a plurality of linear segments. Accordingly, use of the guide 694 results in faceted resection of the femur 698 as indicated by the dashed line 700. This embodiment and others are within the scope of the present invention.

Those of ordinary skill in the art will recognize that the above-described system may be used in a significant number of widely varying procedures. The preceding describes one fairly simple method for incorporating the system of the present invention in a knee replacement surgery in order to show one advantage of the present invention. Those of ordinary skill in the art will appreciate that a number of alternative methods are enabled by the present invention, those alternative methods being within the scope of the present invention.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept. By way of example, but not of limitation, the system described herein may be applied to other bones and joints besides the knee, even joints with a single articulating compartment. Such bones may include tibial and humerus bones.

We claim:

1. A prosthesis system, comprising:
a first component having a first bone contacting surface and a first articulating surface including a first material and opposite to the first bone contacting surface, the first component configured to replace a first portion of a surface of a bone;
a second component having a second bone contacting surface and a second articulating surface opposite to the second bone contacting surface, the second component configured to replace a second portion of the surface of the bone; and
a shapeable shim configured to be placed on the bone at a location between the first component and the second component and having a third bone contacting surface and an outer surface opposite to the third bone contacting surface, the shapeable shim consisting at least mostly of one or more materials, each of the one or more materials softer than the first material.

2. The prosthesis system of claim 1, wherein the shapeable shim is configurable to replace a portion of the surface of the bone.

3. The prosthesis system of claim 2, wherein the shapeable shim comprises:
a flap configured to be placed between a portion of the first bone contacting surface and the bone.

4. The prosthesis system of claim 1, wherein the shapeable shim is attached to the first component pre-operatively.

5. The prosthesis system of claim 4, wherein:
the first component comprises a first side extending between the first bone contacting surface and the first articulating surface; and
the shapeable shim comprises a protuberance extending away from the first side.

6. The prosthesis system of claim 5, wherein the outer surface of the shapeable shim comprises a material which is more resilient than the first material.

7. The prosthesis system of claim 1, wherein the shim comprises a fabric.

8. The prosthesis system of claim 1, wherein:
the first component is a patellofemoral component; and
the second component is a condylar component.

9. A prosthesis system comprising:
a patellofemoral component including a bone contacting surface, an articulating surface opposite to the bone contacting surface, a medial side, and a lateral side and configured to replace a first portion of a patellofemoral surface of a femoral bone;
a first shim configured to be resizable and to replace a second portion of the patellofemoral surface of the femoral bone at a location adjacent to the medial side or the lateral side of the patellofemoral component such that when the patellofemoral component and the first shim are implanted on the femoral bone, the first shim is located medially or laterally of the articulating surface and extends from a surface of the bone along the respective medial side or lateral side of the patellofemoral component and replaces a surface portion of the femoral bone substantially smaller than the first portion of the patellofemoral surface; and a second shim comprising a fabric and configured to replace a third portion of the patellofemoral surface of the femoral bone at a location adjacent to the medial side or the lateral side of the patellofemoral component such that when the patellofemoral component, the first shim, and the second shim are implanted on the femoral bone, the second shim is located on the medial or lateral side of the patellofemoral component opposite to the first shim.

10. The prosthesis system of claim 9, further comprising:
a condylar component configured to replace a portion of a condylar surface of the femoral bone adjacent to the first shim.

11. The prosthesis system of claim 9, wherein the first shim is flexibly connected to the patellofemoral component.

12. A femoral prosthesis system comprising:
a patellofemoral joint component configured to replace a portion of a patellofemoral joint bearing surface and having a first edge extending between a bone contacting surface and an articulating surface of the patellofemoral joint component, the first edge configured to extend generally distally and proximally along a femoral bone when the patellofemoral joint component is implanted on the femoral bone;

a shim having a first edge portion and a second edge portion, the first edge portion configured to be positioned in opposition to the first edge of the patellofemoral joint component so as to extend generally distally and proximally along the first edge of the patellofemoral joint component when the patellofemoral joint component and the shim are implanted on the femoral bone; and a condylar component configured to be located in opposition to the second edge portion of the shim and to replace a portion of a condylar bearing surface of the femoral bone, the shim sizable, and the patellofemoral joint component and the condylar component sized, such that when implanted on the femoral bone the shim replaces a surface area of the femoral bone that is much smaller than the surface area of the femoral bone replaced by either the patellofemoral joint component or the condylar component.

13. The prosthesis system of claim 12, wherein the shim is configured to replace a portion of the surface of the femoral bone.

14. The prosthesis system of claim 13, wherein the shim comprises:
a flap configured to be placed between a portion of the bone contacting surface and the femoral bone when the patellofemoral joint component and the shim are implanted on the femoral bone.

15. The prosthesis system of claim 12, wherein the shim is attached to the patellofemoral joint component pre-operatively.

16. The prosthesis system of claim 15 wherein the shim comprises a protuberance extending away from the first edge of the patellofemoral joint component.

17. The prosthesis system of claim 12, wherein:
the second edge portion is configured to extend generally medially and laterally when the patellofemoral joint component and the shim are implanted on the femoral bone.

18. The prosthesis system of claim 12, wherein the shim is generally wedge shaped.

19. The prosthesis system of claim 12, wherein the first edge portion is configured to be spaced apart from the first edge of the patellofemoral joint component when the patellofemoral joint component and the shim are implanted on the femoral bone.

20. The prosthesis system of claim 10, further comprising:
a filler material.

21. The prosthesis system of claim 12, wherein the shim comprises a fabric.

* * * * *